United States Patent [19]

Pereira

[11] Patent Number: 5,627,262
[45] Date of Patent: May 6, 1997

[54] METHOD AND COMPOSITION FOR THE TREATMENT OF SEPTIC SHOCK

[75] Inventor: Heloise A. Pereira, Edmond, Okla.

[73] Assignee: The Board of Regents of the University of Oklahoma, Norman, Okla.

[21] Appl. No.: 482,328

[22] Filed: Jun. 7, 1995

Related U.S. Application Data

[63] Continuation-in-part of Ser. No. 235,399, Apr. 29, 1994, Pat. No. 5,607,916, which is a continuation-in-part of Ser. No. 969,931, Oct. 30, 1992, Pat. No. 5,458,874, which is a continuation of Ser. No. 855,417, Mar. 19, 1992, Pat. No. 5,484,885, which is a continuation-in-part of Ser. No. 543,151, Jun. 25, 1990, abandoned, which is a continuation-in-part of Ser. No. 375,739, Jul. 5, 1989, abandoned.

[51] Int. Cl.$^6$ .................. C07K 14/00; C07K 14/435; A61K 38/16; A61K 38/17
[52] U.S. Cl. .................. 530/324; 530/300; 424/78.02
[58] Field of Search .................. 424/78.07; 514/12, 514/21; 435/69.1; 530/324

[56] References Cited

U.S. PATENT DOCUMENTS

| | | | |
|---|---|---|---|
| 4,652,639 | 3/1987 | Stabinsky | 435/91.52 |
| 5,087,569 | 2/1992 | Gabay et al. | 435/212 |
| 5,126,257 | 6/1992 | Gabay et al. | 435/212 |
| 5,171,739 | 12/1992 | Scott et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,338,724 | 8/1994 | Gabay et al. | 514/12 |
| 5,447,914 | 9/1995 | Travis et al. | 514/16 |
| 5,458,874 | 10/1995 | Pereira et al. | 424/85.1 |
| 5,484,885 | 1/1996 | Pereira et al. | 530/326 |

OTHER PUBLICATIONS

Ziegler et al., "Treatment of Gram-Negative Bacteremia and Shock with Human Antiserum To A Mutant *Escherichia coli*", *The New England Journal of Medicine*, vol. 307, No. 20, Nov. 11, 1982.

Baumgartner et al., "Prevention of Gram-Negative Shock and Death In Surgical Patients By Antibody to Endotoxin Core Glycolipid", *The Lancet*, Jul. 13, 1985, pp. 59–63.

Brackett et al., "Evaluation of Cardiac Output, Total Peripheral Vascular Resistance, and Plasma Concentrations of Vasopressin in the Conscious, Unrestrained Rat During Endotoxemia", *Circulatory Shock*, 17:273–284, 1985.

Fisher et al., "Initial Evaluation of Human Monoclonal Anti–Lipid A Antibody (HA–1A) in Patients with Sepsis Syndrome", *Critical Care Medicine*, vol. 18, No. 12, 1990, 1311–1315.

Greenman et al., "A Controlled Clinical Trial of E5 Murine Monoclonal IgM Antibody to Endotoxin in the Treatment of Gram–Negative Sepsis", *JAMA*, vol. 266, No. 8, Aug. 28, 1991, pp. 1097–1102 and 1125–1126.

J. Johnston, "Molecular Science Sets Its Sights on Septic Shock", *The Journal of NIH Research*, Vol. 3, Oct. 1991, pp. 61–65.

Ziegler et al., "Treatment of Gram–Negative Bacteremia and Septic Shock With HA–1A Human Monoclonal Antibody Against Endotoxin", *The New England Journal of Medicine*, vol. 324, No. 7, Feb. 14, 1991, pp. 429–436.

"Anti–Endotoxin Monoclonal Antibodies", various editorials, *The New England Journal of Medicine*, vol. 327, No. 12, Sep. 17, 1992, pp. 889–890.

(List continued on next page.)

*Primary Examiner*—Robert A. Wax
*Assistant Examiner*—William W. Moore
*Attorney, Agent, or Firm*—Dunlap & Codding, P.C.

[57] ABSTRACT

The present invention contemplates a composition and method for treating septic shock in a mammal or as a prophylactic treatment prior to a surgical procedure, comprising administering a therapeutically effective amount of a bacterial lipopolysaccharide binding peptide derived from CAP37 protein. In a preferred version, the composition and method of use may comprise a peptide comprising amino acids 20–44 or 120–146 of CAP37 or subunits thereof.

11 Claims, 19 Drawing Sheets

OTHER PUBLICATIONS

C. Welbourn and Y. Young, "Endotoxin, Septic Shock and Acute Lung Injury: Neutrophils, Macprophages and Inflammatory Mediators", *Br. J. Surg.*, vol. 79, Oct. 1992, pp. 998–1003.

W. Ammons and A. Kung, "Recombinant Amino Terminal Fragment of Bactericidal/Permeability–Increasing Protein Prevents Hemodynamic Responses to Endotoxin", *Circulatory Shock*, 41:176–184, 1993.

Pereira et al., "Synthetic Bactericidal Peptide Based on CAP37: A 37kDa Human Neutrophil Granule–Associated Cationic Antimicrobial Protein Chemotactic for Monocytes", *Proc. Natl. Acad. Sci. USA*, vol. 90, pp. 4733–4737, May 1993.

S. Aldridge, "Meeting the Challenge of Sepsis", *TIBTECH*, vol. 11, Sep. 1993.

W. Hoffman, and C. Natanson, "Endotoxin in Septic Shock", *Anesth Analg*, 1993;77:613–24.

Dialog(R) file 155 Accession number 93226936, Offenstadt, G. et al., Jan. 1, 1993. "Therapeutic Perspectives of Severe Infectious States", *REV PRAT* (France), vol. 43, No. 1, pp. 59–64, Abstract Only.

Cross et al., Jul. 1993, "Choice of Bacteria in Animal Models of Sepsis", *Infection and Immunity*, vol. 61, No. 7, pp. 2741–2747.

Embase No. 94208915, Rogy et al., 1994, "Anti–endotoxin Therapy in Primate Bacterium With HA–1A and BPI", *ANN SURG* (USA), vol. 220, No. 1, pp. 77–85, Abstract Only.

Stewart et al., "Comparison of *Staphylococcus aureus* and *Escherichia coli* Infusion in Conscious Rats", *Journal of Surgical Research*, 56, 60–66, 1994.

J. Gabay, "Ubiquitous Natural Antibiotics" *Science*, vol. 264, 15 Apr. 1994, pp. 373–374.

Embase No. 95085016, Hurley, J.C., 1995. "Endotoxaemia and Novel Therapies for the Treatment of Sepsis", *Expert Opinion on Investigational Drugs* (United Kingdom), vol. 4, No. 3, pp. 163–174, Abstract Only.

METHOD AND COMPOSITION FOR THE TREATMENT OF SEPTIC SHOCK

Some aspects of this invention were made in the course of Grant AI 28018 awarded by the National Institutes of Health and therefore the Government has certain rights in some aspects of this invention.

CROSS REFERENCE TO RELATED APPLICATIONS

This application is a continuation-in-part of U.S. Ser. No. 08/235,399, filed Apr. 29, 1994, and issued as U.S. Pat. No. 5,607,916 on Mar. 4, 1997, which is a continuation-in-part of U.S. patent application Ser. No. 07/969,931, filed Oct. 30, 1992, and issued as U.S. Pat. No. 5,458,874 on Oct. 17, 1995, which is a continuation of U.S. Serial No. 07/855,417, filed Mar. 19, 1992, and issued as U.S. Pat. No. 5,484,885 on Jan. 16, 1996, which is a continuation-in-part of U.S. Ser. No. 07/543,151, filed Jun. 25, 1990, and now abandoned, which is a continuation-in-part of U.S. Ser. No. 07/375,739, filed Jul. 5, 1989, now abandoned. The specification and sequence listing of each of the above applications is hereby incorporated herein by reference.

BACKGROUND

Septic shock (also known as sepsis) causes more than 150,000 deaths annually in the United States. Sepsis is defined as a clinical disorder whose symptoms may include well defined abnormalities in body temperature, heart rate, breathing rate, white blood cell count, hypotension, organ perfusion abnormalities, and multiple organ dysfunction. It may be caused by bacterial (either gram negative or gram positive), fungal, viral and other infections as well as by non-infective stimuli such as multiple trauma, severe burns, organ transplantation and pancreatitis. In Europe there are 500,000 cases annually with a lethal outcome of 40–70%. Even with improved patient management the mortality rate ranges from 50% to 75% in patients with established septic shock. There has not been a significant decrease in this mortality rate since the advent of broad spectrum antibiotics in the early 1960s. Septic patients usually die as a result of poor tissue perfusion and injury followed by multiple organ failure. It is now generally accepted that a significant portion of the peripheral responses occurring during septic shock are initiated by endotoxin. Endotoxin (also referred to herein as lipopolysaccharide, bacterial lipopolysaccharide or LPS), an outer membrane component of gram-negative bacteria, is released upon the death or multiplication of the bacteria. Administration of endotoxin to experimental animals elicits a series of sequential cardiovascular, metabolic, and pathologic responses culminating in organ dysfunction and failure, ultimately resulting in death. When endotoxin is administered to normal human subjects, physiologic, biochemical, and cellular responses are induced that quantitatively mimic those occurring during septic shock. However, it is becoming increasingly recognized that the majority of responses observed during sepsis and endotoxemia are not due to direct actions of endotoxin, but result from endotoxin induction of a myriad of cellular and humoral inflammatory mediators. Furthermore, even with the vast research and clinical literature regarding sepsis and endotoxemia, there is no definitive regimen for the treatment of septic shock with the thrust of therapy being targeted at correction of symptoms.

Clinicians are dissatisfied with the existing therapies for septic shock which currently consist of antibiotic therapy or hemodynamic and metabolic support. The intravenous antibiotics eradicate the bacteria and the fluid infusion attempts to reverse the hypotension.

The impact of sepsis and any situation of endotoxemia is particularly devastating to patients with compromised cardiac and hepatic function and to immunocompromised patients. Patients at high risk are the elderly (an increasing percentage of our society), chemotherapy patients, and those requiring surgery or invasive instrumentation. The current therapy of antibiotics and hemodynamic support has not proven to be successful. Experimental studies have indicated that antibodies to certain cytokines may ameliorate some, but not all of the manifestations of the sepsis syndrome. There is such an explosion of physiological responses and release of mediators during septic shock that the antagonism of a single mediator may not always be effective.

Although septic shock can follow any bacterial infection, it is most often the sequel to a gram negative infection. Klebsiella, Pseudomonas, *Escherichia coli*, Bacteroides and Salmonella are the most frequent cause.

Septic shock usually begins with tremor, fever, falling blood pressure, rapid breathing and heart beat, and skin lesions. Within hours or days it can progress to spontaneous clotting in the blood vessels, severe hypotension, multiple organ failure and death.

Most of the damage comes not from the invading bacteria but from endotoxin. The component responsible for the toxic effect of the LPS molecule is the lipid component, called lipid A. This region is buried in the outer membrane of the bacterium and is believed to be reasonably constant between different species of gram negative bacteria. The polysaccharide region of the molecule extends from the surface of the bacterium and is different for each bacterial strain. The polysaccharide region consists of an inner core region composed of a heptose, and a 3, deoxy-D-manno-2-octulosonic acid (KDO) molecule. The KDO molecule is found in all lipopolysaccharide and links the polysaccharide to the lipid A moiety.

The manner in which endotoxin evokes its effects is by binding to cells such as monocytes/macrophages or endothelial cells, and triggering them to produce various mediator molecules such as toxic oxygen radicals, hydrogen peroxide, tumor necrosis factor-alpha (TNF-$\alpha$), various interleukins (IL-1, IL-6, and IL-8). Endotoxin in even the very smallest amounts can activate these cells.

Depending on the dose or concentration of endotoxin, the effects may either be deleterious or advantageous to the host. If excessive TNF-$\alpha$, IL-1, IL-6, and IL-8 are produced, they can evoke endotoxic (or septic) shock with symptoms ranging from chills and fever to circulatory failure, multiorgan failure, and death. An improved method of treating or preventing septic shock would be of great value.

DESCRIPTION OF THE INVENTION

Figure 1:
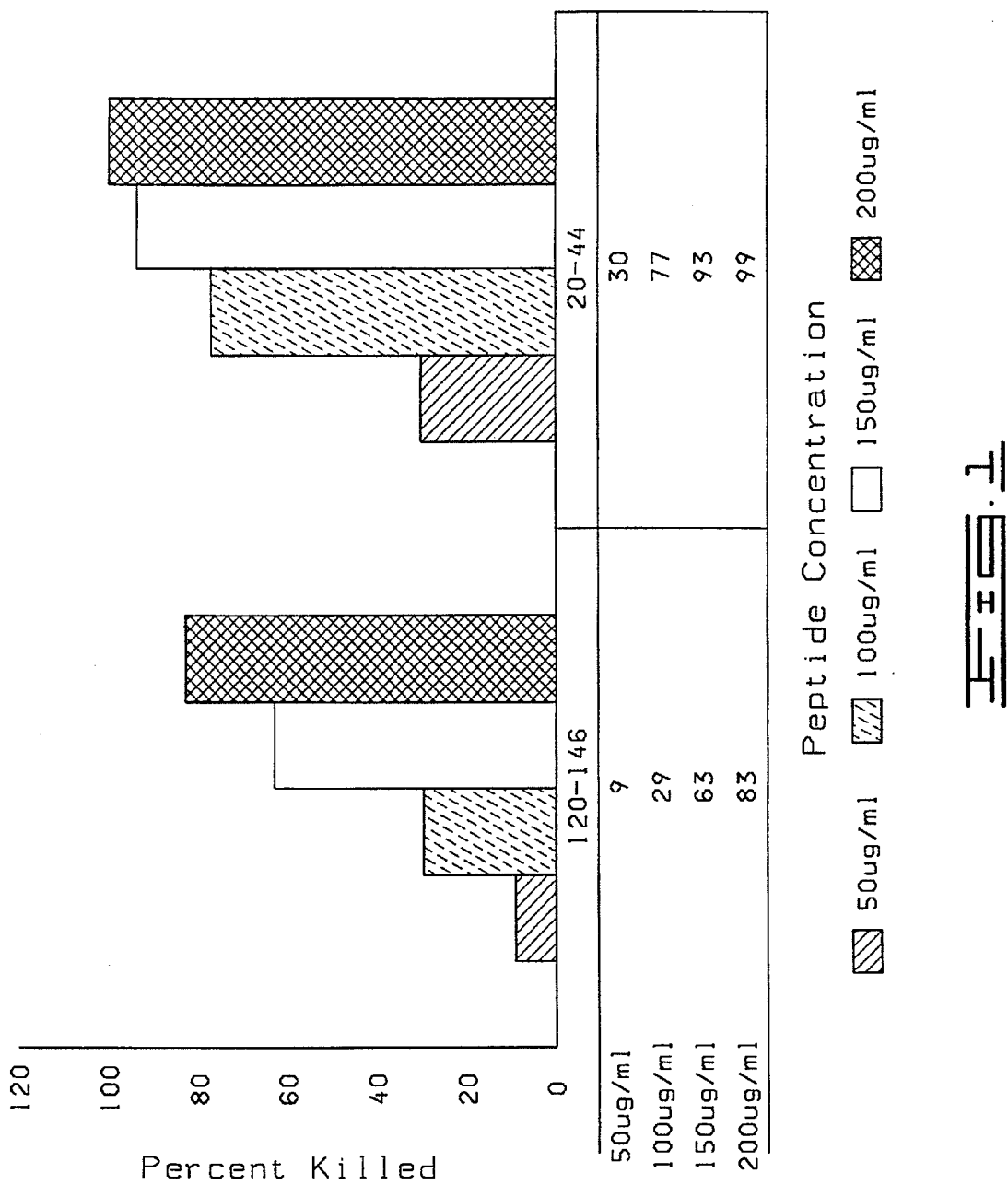
FIG. 1 is a graph comparing the bactericidal effects of peptides 120–146 and 20–44.

A naturally occurring protein called CAP37 (Cationic Antimicrobial Protein having a molecular weight of 37 kD) has been shown to be a multifunctional protein, with extremely important functions in host defense and inflammation. Not only does CAP37 have antibiotic activity but it is also a very potent chemoattractant for monocytes, can bind heparin, and has the capacity to bind endotoxin or lipopolysaccharide. The protein can be isolated from human neutrophils and is present in the granules of those cells. It has been purified to homogeneity, and it migrates on SDS-PAGE as a 37 kD protein. Further details of the amino acid sequence and purification of the protein and peptides derived from the protein can be found in copending U.S. Ser. No. 07/969,931, filed Oct. 30, 1992 and in the article "Synthetic Bacterial Peptide Based On CAP37: A 37-kDa Human Neutrophil Granule-Associated Cationic Antimicrobial Protein Chemotactic For Monocytes", H. A. Peteira, I. Erdem, J. Pohl, and J. Spitznagel, *Proc. Natl. Acad. Sci. USA*, 90: 4733–4737, May 1993, which is hereby incorporated herein by reference.

The present invention contemplates a composition for treating septic shock in a mammal, comprising a therapeutically effective amount of a peptide derived from CAP37 protein. In a preferred version, the composition may comprise a peptide having the amino acid sequence as defined in the Sequence Listing of SEQ ID NO:1. In another version of the invention, the composition may comprise a peptide comprising a subunit of the amino acid sequence defined in the Sequence Listing of SEQ ID NO:1, for example, having the amino acid sequence as defined in the Sequence Listing of SEQ ID NO:2. In another version of the invention, the composition may comprise a peptide having the amino acid sequence as defined in the Sequence Listing of SEQ ID NO:3, or an effective subunit thereof.

The invention further contemplates a peptide capable of binding to bacterial lipopolysaccharide, comprising the amino acid sequence as defined in the Sequence Listing of SEQ ID NO:1 or SEQ ID NO:3 or effective subunits thereof. The invention further contemplates a DNA molecule comprising a DNA sequence coding for a peptide derived from the 20th to 44th amino acid region of CAP37 as defined in the Sequence Listing by SEQ ID NO:1, or an effective subunit thereof, the peptide coded therefor effective in binding to bacterial lipopolysaccharide. In another version, the invention is a DNA molecule comprising a DNA sequence coding for a peptide derived from the 120th to 146th amino acid region of CAP37 as defined in the Sequence Listing of SEQ ID NO:3, or an effective subunit thereof, the peptide coded therefor effective in binding to bacterial lipopolysaccharide.

The invention further contemplates a method for treating septic shock in a mammal, comprising administering to the mammal a therapeutic composition comprising a pharmacologically effective amount of a bacterial lipopolysaccharide binding peptide derived from CAP37 protein (the term "bacterial lipopolysaccharide binding peptide" when used herein is meant to refer to a peptide derived from CAP37 protein and is not meant to be confused with the polypeptide known in the art as "Lipopolysaccharide Binding Protein"). In a preferred embodiment of the method, the peptide derived from CAP37 has the amino acid sequence as defined in the Sequence Listing by SEQ ID NO:1 or an effective subunit thereof. In an alternate embodiment of the method, the peptide derived from CAP37 has the amino acid sequence as defined in the Sequence Listing by SEQ ID NO:2. In another version of the method, the peptide has the amino acid sequence as defined in the Sequence Listing by SEQ ID NO:3, or an effective subunit thereof.

The invention further contemplates a method of prophylactic treatment for preventing septic shock in a mammal, comprising administering to the mammal a therapeutic composition comprising a pharmacologically effective amount of a lipopolysaccharide binding peptide derived from CAP37 protein. In a preferred embodiment of the method, the peptide derived from CAP37 has the amino acid sequence as defined in the Sequence Listing by SEQ ID NO:1. In an alternate version of the invention, the peptide derived from CAP37 has the amino acid sequence as defined in the Sequence Listing by SEQ ID NO:2. In another version of the method, the peptide has the amino acid sequence as defined in the Sequence Listing by SEQ ID NO:3, or an effective subunit thereof.

The present invention further contemplates a method of treating physiological effects induced by bacterial lipopolysaccharide in a mammal, for example on systemic vascular resistance, cardiac output, tissue perfusion, and white blood cell count, comprising administering to the mammal a therapeutic composition comprising a pharmacologically effective amount of a bacterial lipopolysaccharide binding peptide derived from CAP37 protein. In a preferred embodiment of the method, the peptide derived from CAP37 has the amino acid sequence as defined in the Sequence Listing by SEQ ID NO:1. In an alternate version of the invention, the peptide derived from CAP37 has the amino acid sequence as defined in the Sequence Listing by SEQ ID NO:2. In another version of the method, the peptide has the amino acid sequence as defined in the Sequence Listing by SEQ ID NO:3, or an effective subunit thereof.

The present invention further contemplates a method of mediating or preventing the effects of a bacterial lipopolysaccharide-induced response in a test animal, comprising the steps of providing a test animal, administering a predetermined amount of endotoxin to the test animal, and administering a predetermined amount of CAP37 peptide 20–44 to the test animal or an effective subunit thereof, or a predetermined amount of CAP37 peptide 120–146, or an effective subunit thereof.

The invention further includes a method of treating a wound by the application of a topical medication containing a cationic granule protein (CAP37) having the amino acid sequence shown in the Sequence Listing as SEQ ID NO:3, or proteins and/or peptides derived from CAP37 that are chemotactic for monocytes or possess antibacterial activity, in the medication in a pharmacologically effective amount to promote wound healing and/or treat infection. Other additions to the medication may be desirable such as the inclusion of epidermal growth factor also present in a pharmacologically effective amount to promote wound healing. The topical medication may take any number of standard forms such as pastes, gels, creams, and ointments. Additionally, the invention includes methods of treating tumors and other diseases using CAP37 and its related proteins and peptides.

It is an object of this invention to treat infection, especially infection caused by gram negative bacteria, by administration of an effective amount of a peptide derived from CAP37 having bactericidal activity superior to that of the mature CAP37 protein, most preferably by administration of the peptide defined in the Sequence Listing by SEQ ID NO:3.

Antibiotic Activity of CAP37 Peptides 20–44 and 120–146

Some of the results of Pereira, et al. 1993 are summarized below. A peptide NQGRHFCGGALIHARFVMTAASCFQ corresponding to residues 20–44 of the mature CAP37 protein has been shown to have strong antimicrobial activity (for the sequence of peptide 20–44, see Seq. ID No. 1 of the present application which corresponds to Seq. ID No. 8 in U.S. Ser. No. 07/969,931). Various overlapping peptides corresponding to the amino acid sequences 1–25, 20–44, 38–53, 43–53, 72–80, 95–122, 102–122, 113–122, 130–146, and 140–165 of the native CAP37 protein were synthesized. All peptides were assayed for bactericidal activity using Salmonella typhimurium SH9178 as the test organism. It was apparent that one of the peptides, peptide 20–44, had significantly greater antibiotic activity than the other peptides tested (FIG. 1 in Pereira et al., 1993). Almost one hundred percent (99.3%) of the bacteria were killed at the highest concentration tested and 90% of killing was achieved at 100 µg/ml concentration of the peptide. Various substitutions and truncations of peptide 20–44 indicated that peptide 20–44 was by far the most active. Particularly interesting was an analog of peptide 20–44 in which the cysteines at positions 26 and 42 were substituted with serines. This serine-substituted peptide was inactive in our bactericidal assays.

The comparative bactericidal effects of peptides 120–146 and 20–44 are shown in FIG. 1. The standard bactericidal assay using Salmonella typhimurium SH9178 was used, as above. At 200 µg/ml of peptide 120–146, for example, 83% of bacteria are killed while 99% of bacteria are killed by peptide 20–44. The relationship is dose dependent.

As noted above, the present invention is a method for using a composition comprising a CAP37 peptide in the treatment of sepsis. The use of CAP37 peptide 20–44 or 120–146 would not only be confined to patients who had already developed endotoxemia, but could also be used prophylactically before any bowel or bladder surgery or manipulations of other organs where gram negative bacteria normally reside and create the risk of entry into the bloodstream and the subsequent induction of sepsis. The present invention also contemplates using CAP37 peptide 23–42, a subunit of peptide 20–44, (for the sequence of peptide 23–42, see Seq. ID No. 2 in the present application, which corresponds to Seq. ID No. 7 in U.S. Ser. No. 07/969,931) and an effective subunit of 120–146 in the treatment of sepsis.

Figure 2:
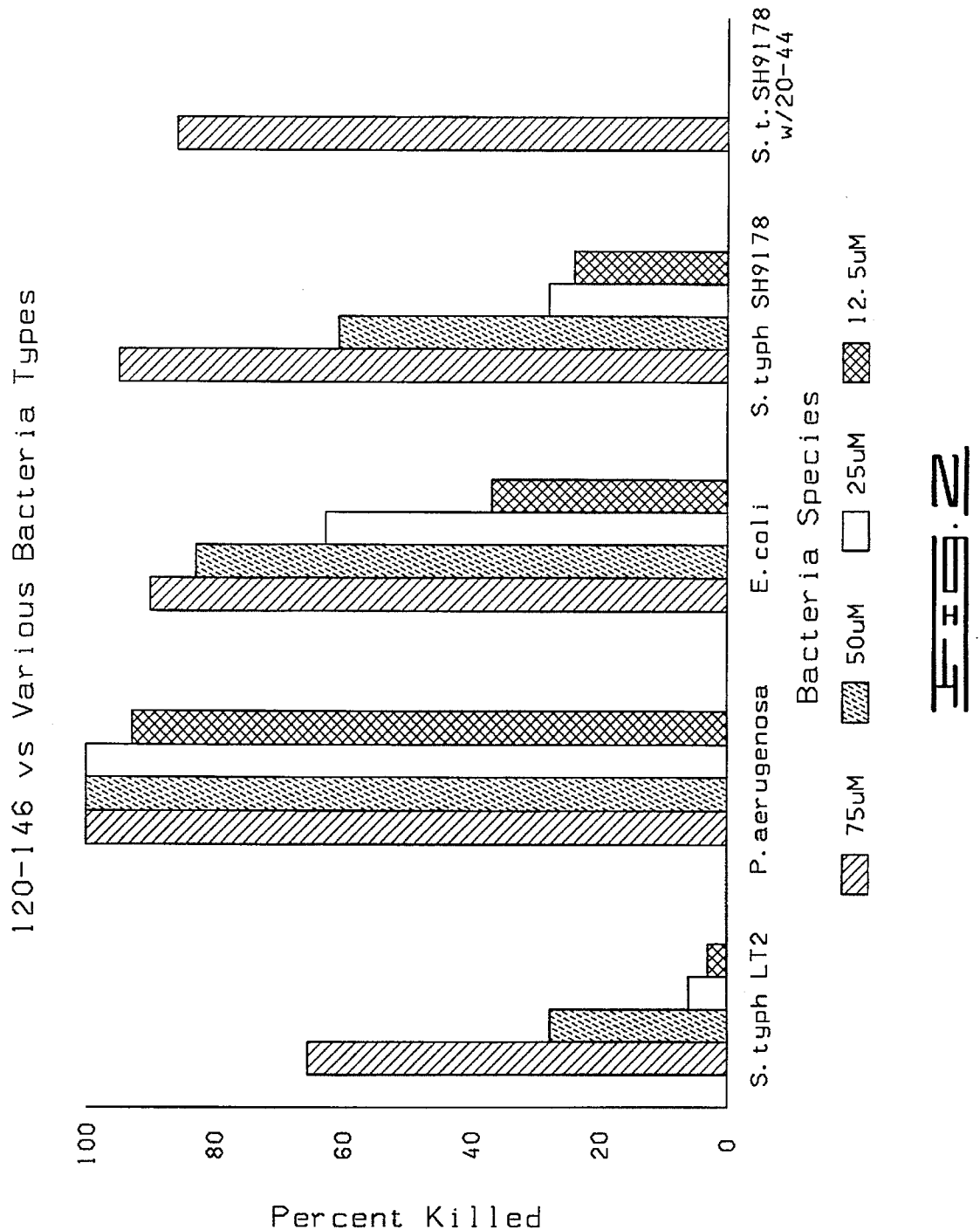
FIG. 2 is a graph showing the effects of several concentrations of CAP peptide 120–146 against several species of bacteria.
Figure 14:
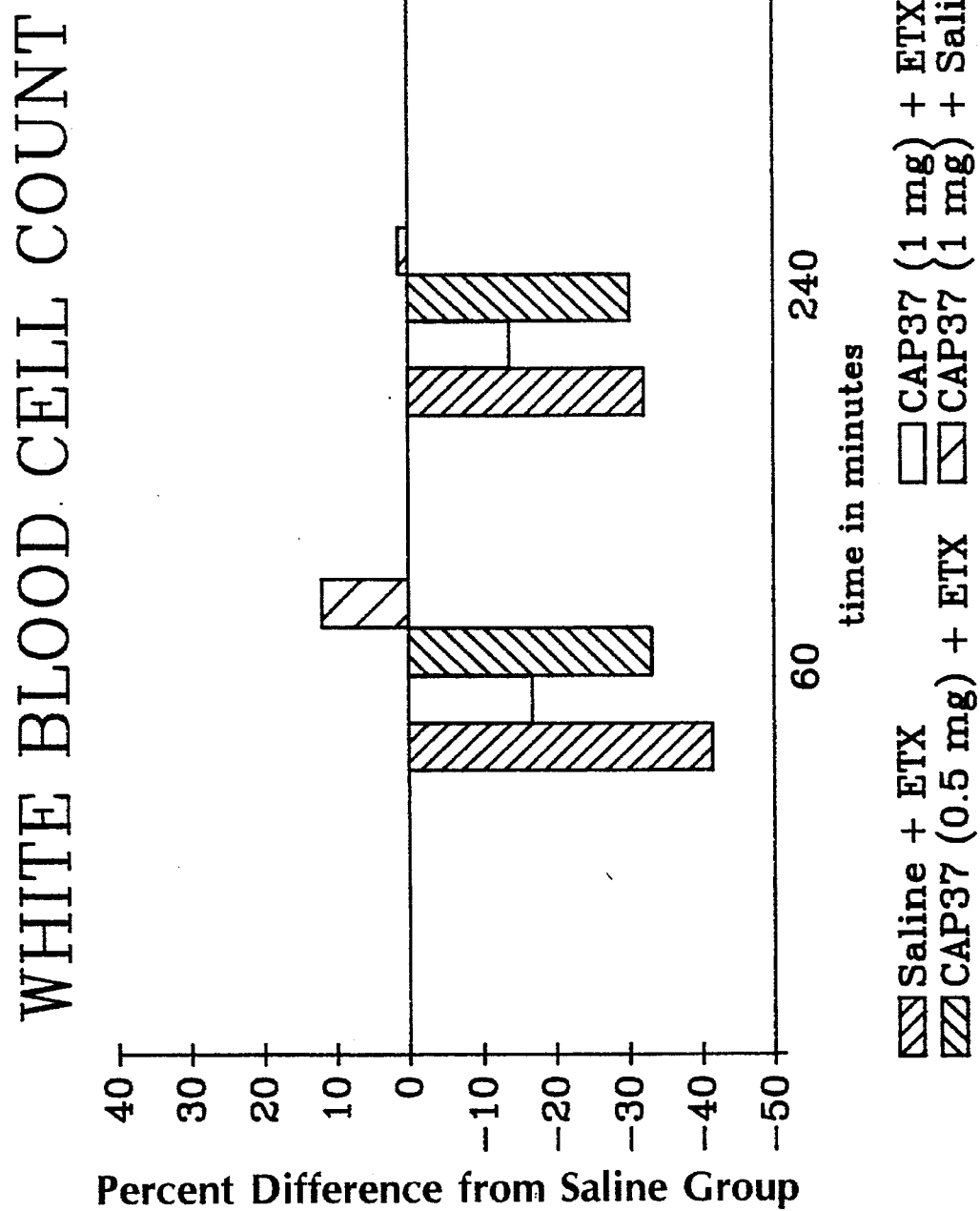
FIG. 14 is a graph comparing the effects of endotoxin and CAP37 peptide 20–44 on white blood cell count in the hyperdynamic model of septic shock.
Figure 15:
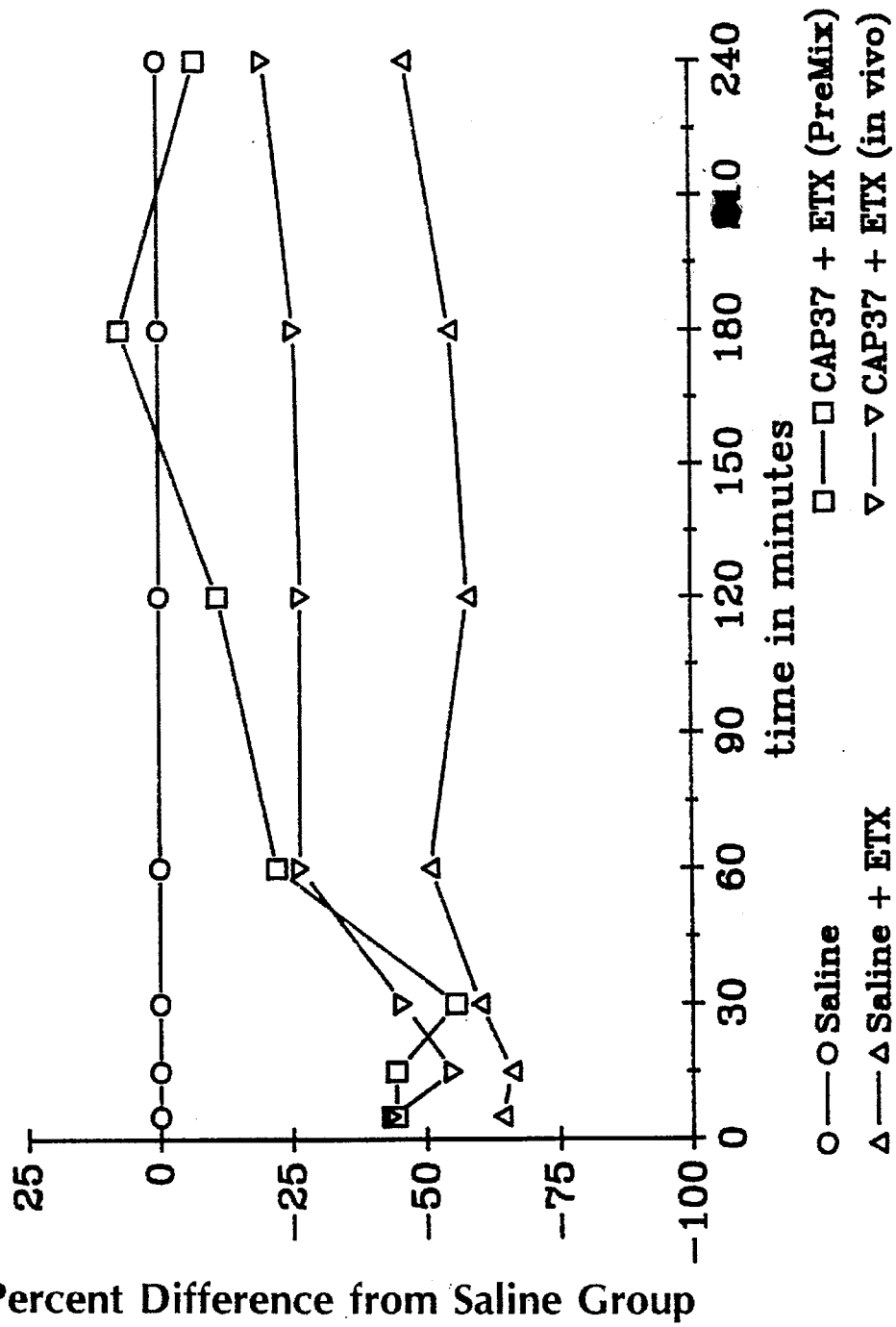
FIG. 15 is a graph comparing the effects of endotoxin and CAP37 peptide 20–44 on cardiac index in the hypodynamic model of septic shock.
Figure 16:
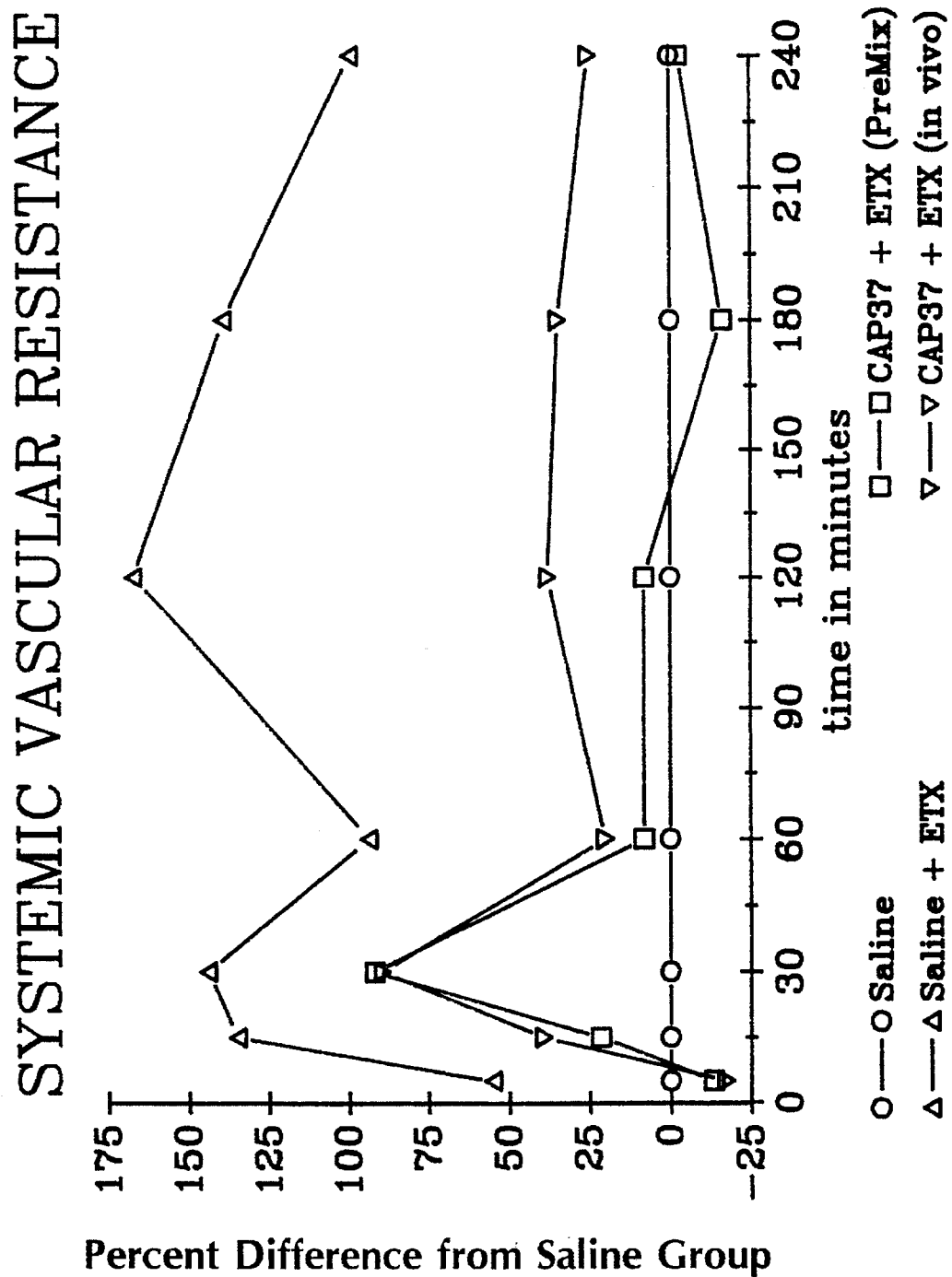
FIG. 16 is a graph comparing the effects of endotoxin and CAP37 peptide 20–44 on systemic vascular resistance in the hypodynamic model of septic shock.
Figure 17:
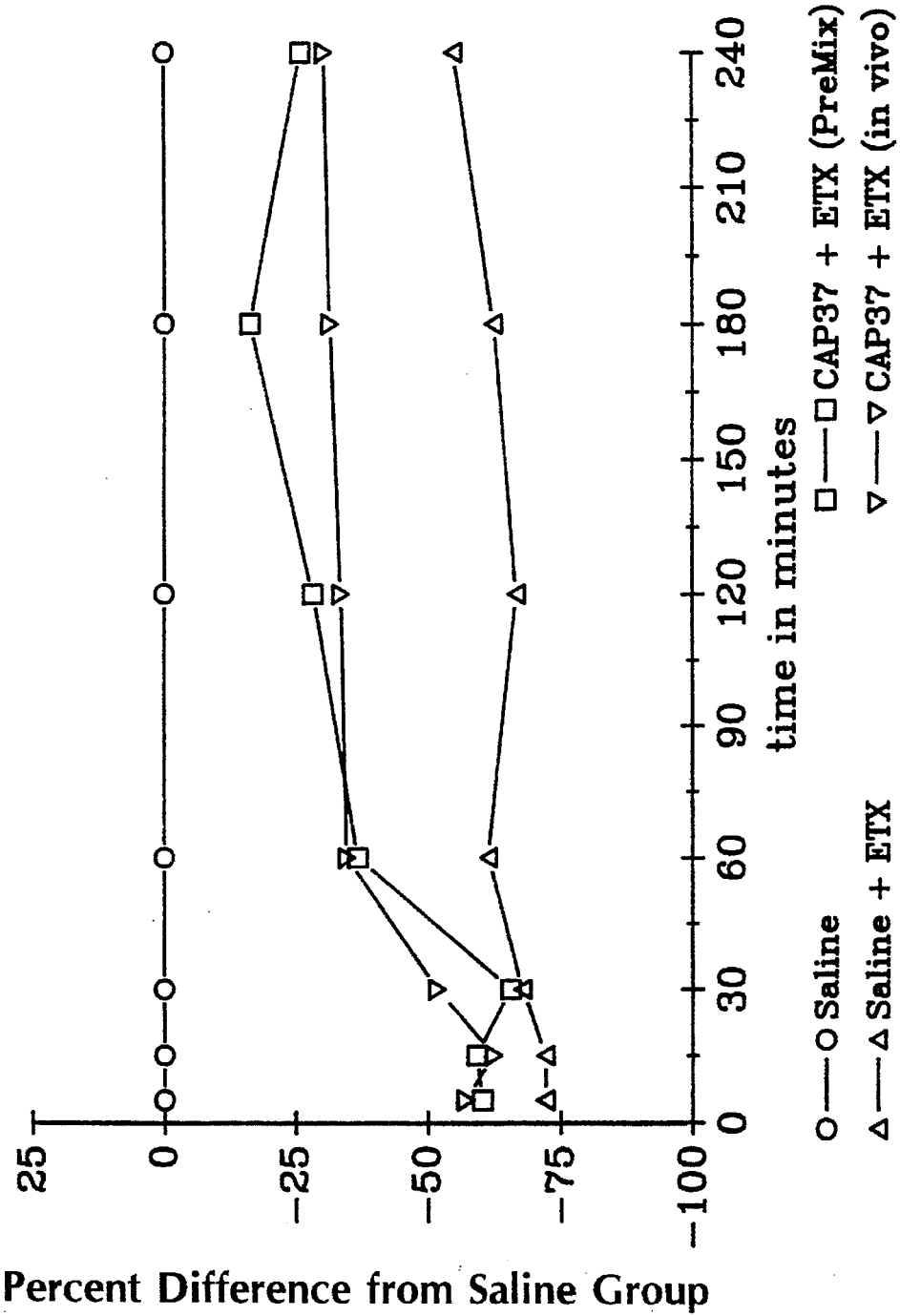
FIG. 17 is a graph comparing the effects of endotoxin and CAP37 peptide 20–44 on cardiac stroke volume in the hypodynamic model of septic shock.

Bactericidal Activity of CAP37 Peptides 20–44 and 120–146 Against Various Bacterial Strains The bactericidal activity of peptide 20–44 was evaluated against a number of gram negative and gram positive bacteria (FIG. 14 in U.S. Ser. No. 07/855,417) and against various strains of Salmonella typhimurium with a range of endotoxin chemotypes and various clinical isolates of S. typhimurium designated with the prefix C (FIG. 2 in Pereira et al., 1993). Of the various organisms tested, Pseudomonas aeruginosa, Escherichia coli, and Enterococcus faecalis were highly sensitive to the action of CAP37. Significantly, peptide 20–44 has enhanced bactericidal activity compared to the native CAP37 protein. Previous evidence strongly indicated native CAP37 has a fairly narrow spectrum of bactericidal activity, being primarily effective against gram negative bacteria such as S. typhimurium, E. coli, P. aeruginosa, S. typhi, and Shigella sonnei. Most interestingly the activity of peptide 20–44 is not limited in its action to gram negative bacteria alone. It is particularly active against E. faecalis and shows moderate activity against Staphyloccus aureus, which is resistant to native CAP37. Other gram positive organisms such as Listeria monocytogenes and Streptococcus pyrogenes are resistant to the activity of the 20–44 peptide. All strains of Proteus tested and Morganella morganii are resistant to the peptide 20–44. The moderate activity of peptide 20–44 against S. aureus indicates that it may be useful in treating septic shock caused by S. aureus and possibly other gram positive bacteria.

The microbicidal activity of peptide 20–44 parallels the activity of the native CAP37 protein regarding the effect on various strains of S. typhimurium with a range of LPS chemotypes. In general, the smooth strains of Salmonella are more resistant and the rough strains more sensitive. A polymyxin B resistant strain (pmrA) of Salmonella (SH7426) was cross resistant to peptide 20–44 as it was to CAP37. Resistance to peptide 20–44 conferred by pmrA compensated remarkably well for the decrease in resistance due to rough, Rb chemotype due to the rfaJ mutation. The six clinical isolates of S. typhimurium showed various levels of sensitivity.

Thus, there is substantial data that peptide 20–44 mimics the potent antimicrobial activity of the native protein CAP37 but appears to have a broader spectrum of action since it is also active on gram positive organisms. Peptide 20–44 is antimicrobial at concentrations of $1.25–7.5\times10^{-5}$, as are other antibiotic peptides such as the defensins. Peptide 20–44 appears to be maximally active between pH 5 and pH 5.5. The two cysteine residues at positions 26 and 42 are required for bactericidal activity suggesting that disulfide bond formation may be important for antimicrobial action. Analysis of the activity of several related peptides indicates that a combination of features such as hydrophobicity (56% of its amino acid residues are hydrophobic), basic charge, and relatively small size facilitates its interaction with lipid A on the surface of gram negative organisms, and may be the basis for its antibacterial activity.

Figure 3:
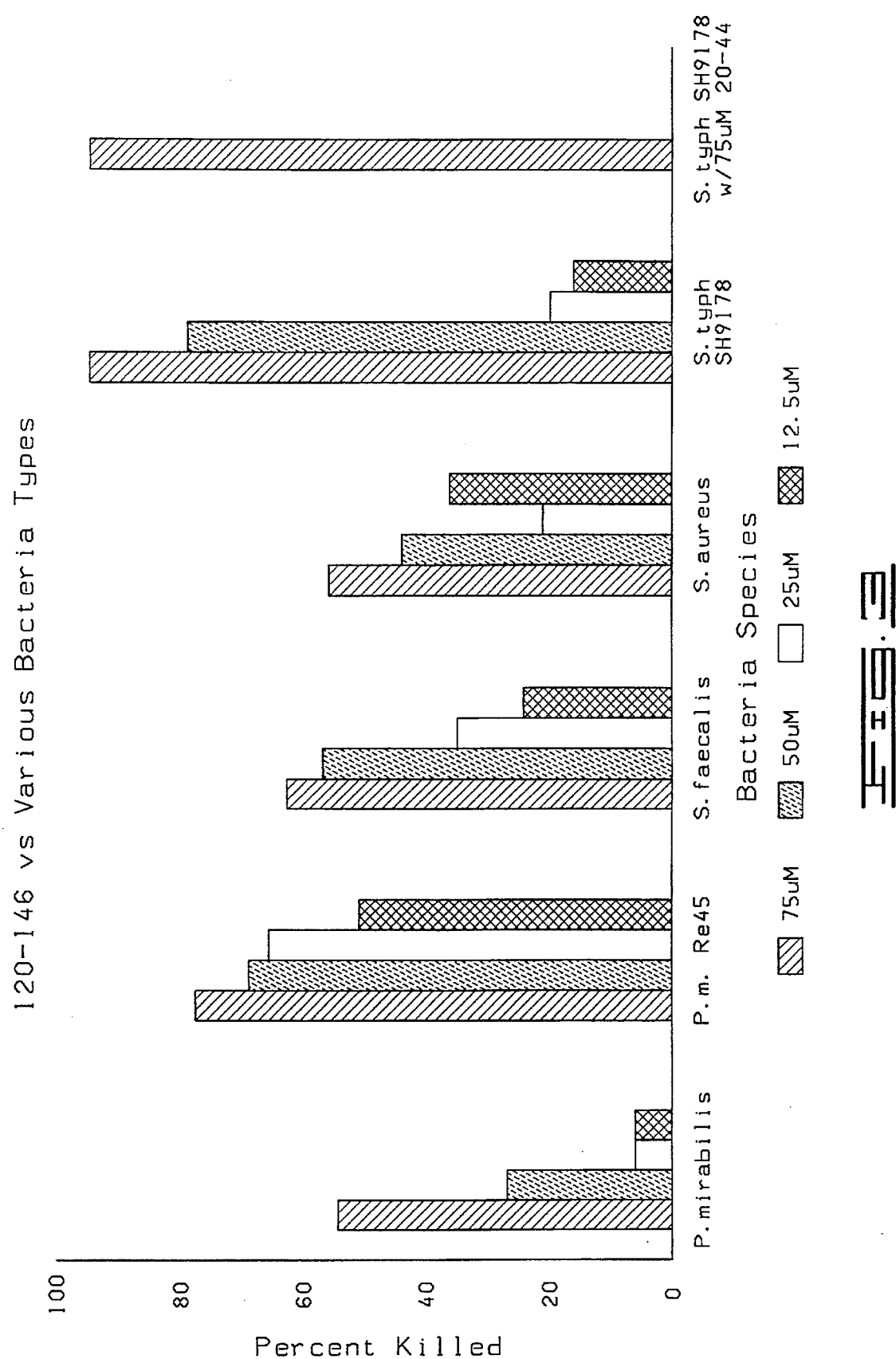
FIG. 3 is a graph showing the effects of several concentrations of CAP peptide 120–146 against several additional species of bacteria.
Figure 4:
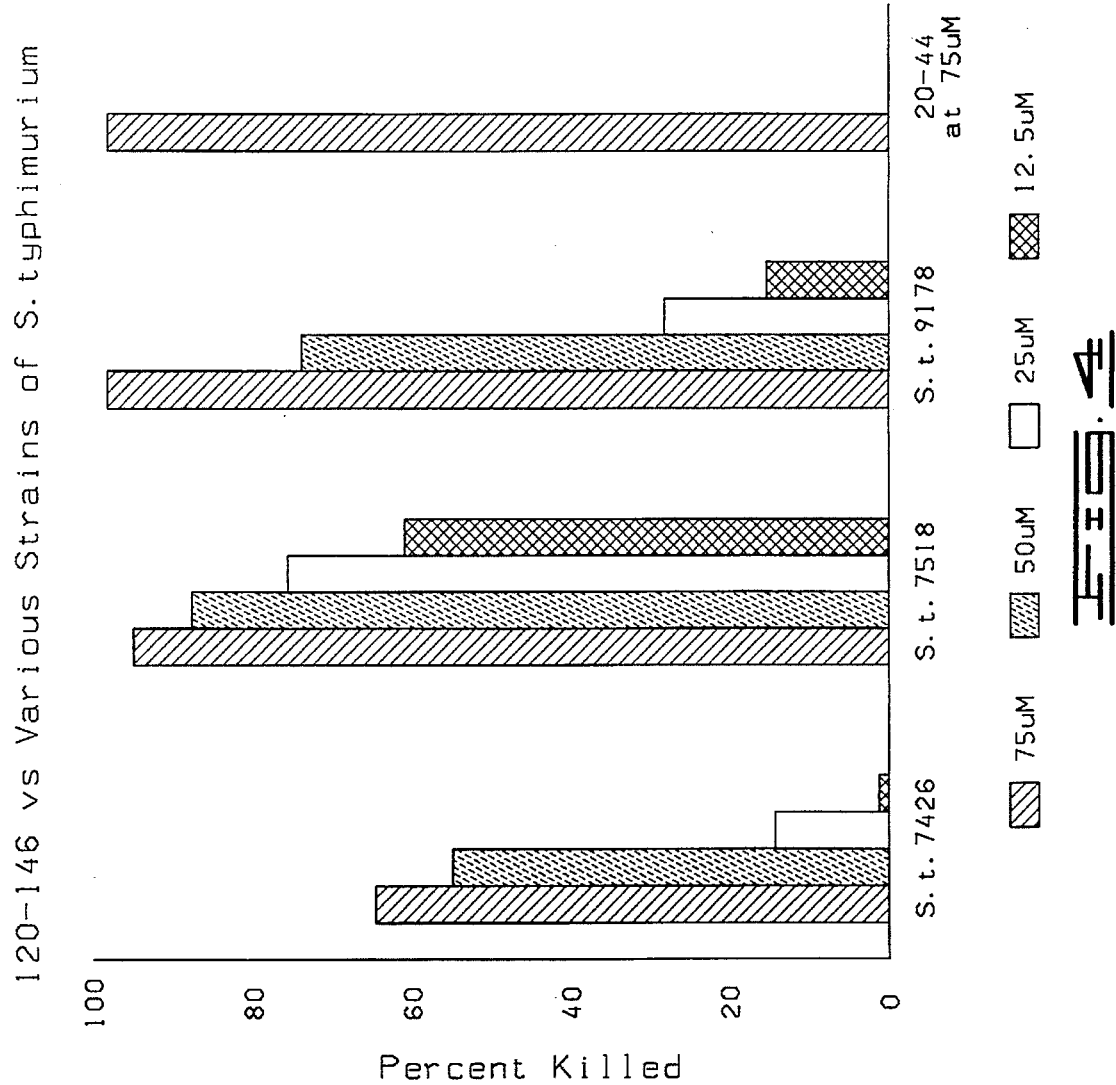
FIG. 4 is a graph showing the effects of several concentrations of CAP peptide 120–146 against various strains of *Salmonella typhimurium*.

The bactericidal activities of CAP37 peptide 120–146 against a number of other bacterial species are shown in FIGS. 2–4. FIG. 2 shows the activity of peptide 120–146 against wild type Salmonella typhimurium LT2, Pseudomonas aeruginosa, and E. coli. FIG. 3 shows activity of peptide 120–146 against Proteus mirabilis (wild type), P. mirabills Re45, S. faecalis, and Staphylococcus aureus. FIG. 4 shows activity of peptide 120–146 against Salmonella typhimurium 7426, S. typhimurium 7518 and S. typhimurium 9178. The results indicate that peptide 120–146 is variably active against all bacterial strains tested.

Lipopolysaccharide Binding Activity of CAP37

Native CAP37 binds to endotoxin. An ELISA was used to determine binding of native CAP37 to various preparations of LPS and lipid A. The microtitre plate was coated with LPS from S. minnesota wild type, LPS from S. minnesota Re mutant, lipid A from S. minnesota wild type R595, and lipid A from S. typhimurium Re mutant at concentrations ranging from 0 to 50 µg/ml and incubated overnight. After careful washing, the plates were incubated with 120 ng per well of CAP37. A monospecific rabbit anti CAP37 antibody was then applied to the plates, and development of the ELISA was performed as previously published in Peteira, et al., "Quantitation of a Catonic Antimicrobial Granule Protein of Human Polymorphonuclear Leukocytes by ELISA", J. Immuno. Methods, 117: 115–120, 1989 (and in FIG. 3 in U.S. Ser. No. 07/855,417) which is hereby incorporated herein by reference. The results described therein and here support the hypothesis that CAP37 is able to bind endotoxin, and in particular the lipid A moiety.

Figure 5:
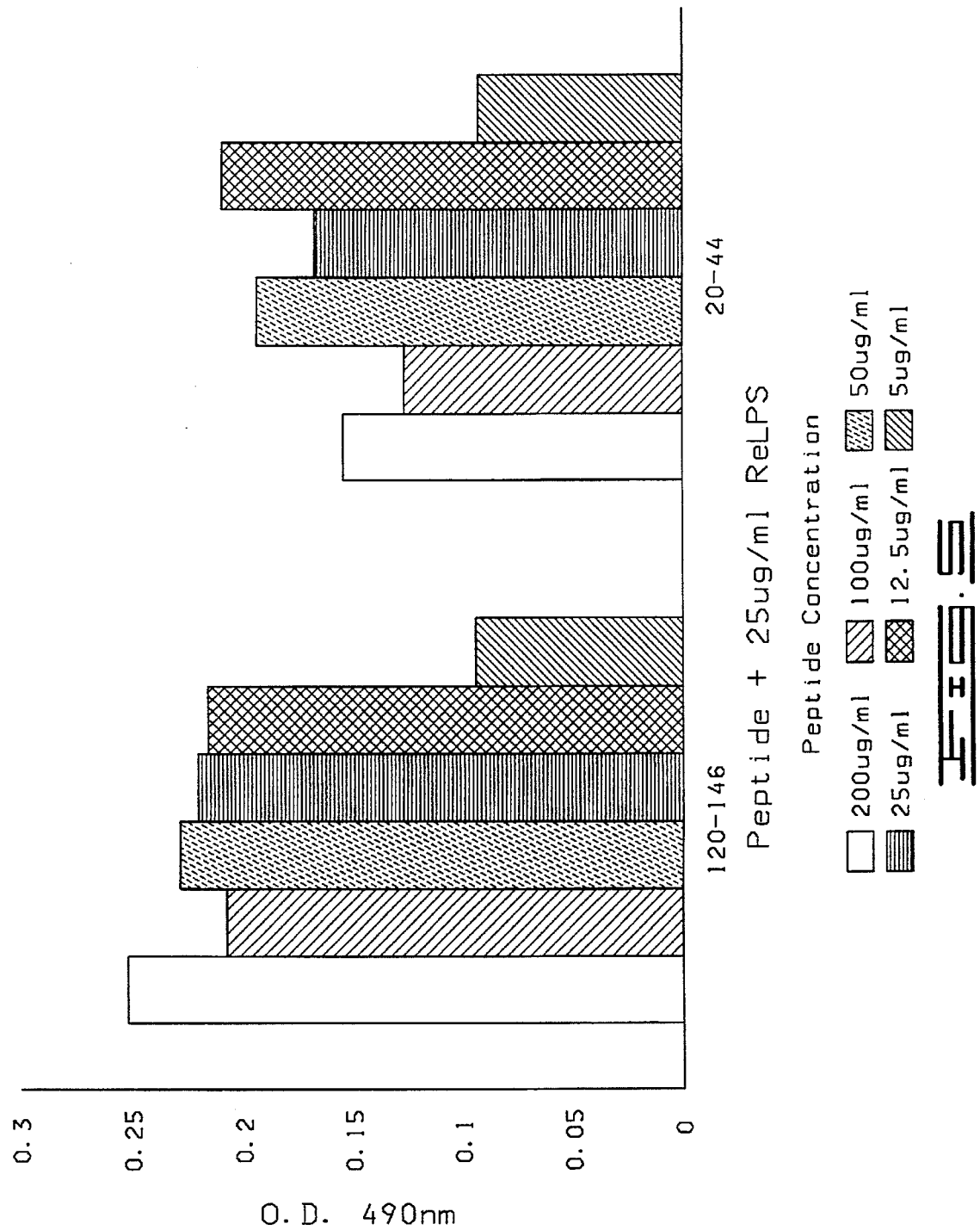
FIG. 5 is a graph showing the binding of peptides 120–146 and 20–44 to ReLPS.

The ability of CAP37 peptides 20–44 and 120–146 to bind to ReLPS using the ELISA technique is shown in FIG. 5. The concentration of ReLPS is constant at 25 µg/ml. The concentrations of the peptides are varied from 200, 100, 50, 25, 12.5 and 5 µg/ml. The peptide 120–146 binds ReLPS in a dose-dependent fashion.

Lipopolysaccharide Neutralization and Binding by CAP37 and Peptides 20–44 and 120–146

Figure 6:
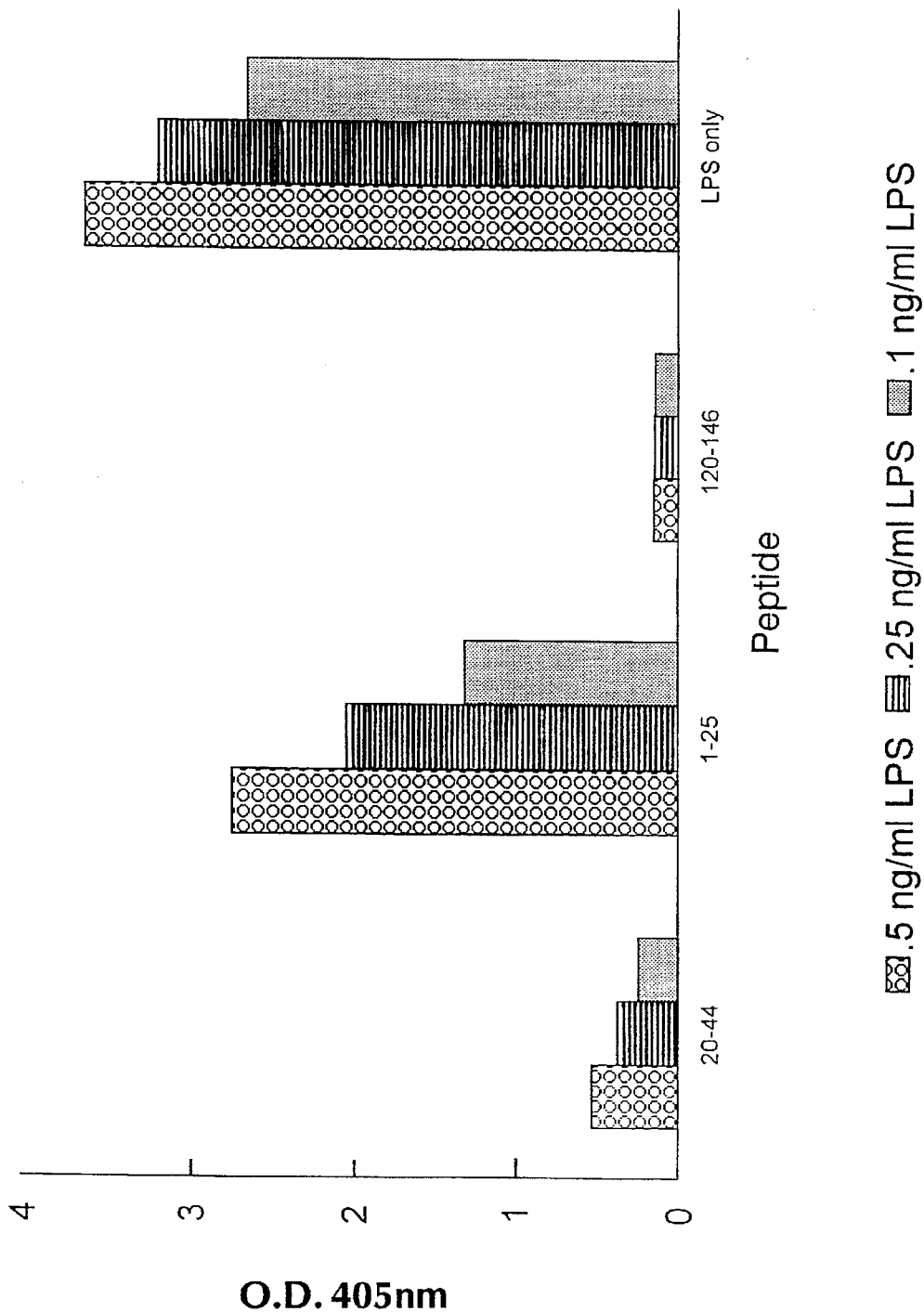
FIG. 6 is a graph comparing the effects of various CAP37 peptides on the neutralization of LPS.
Figure 8:
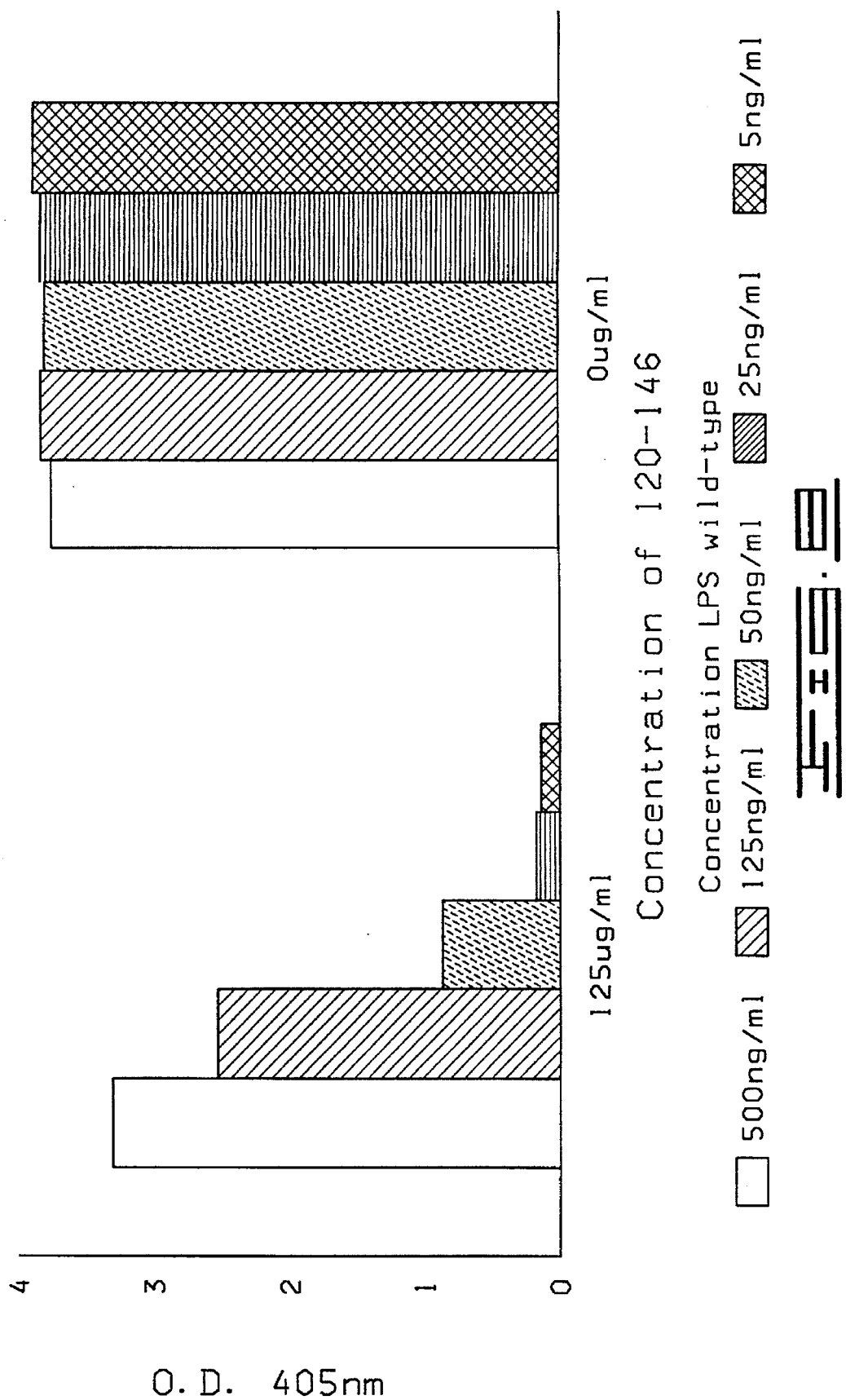
FIG. 8 is a graph showing the neutralizing effects of peptide 120–146 against various concentrations of LPS.

It was found that the bactericidal action of CAP37 peptide 20–44 could be inhibited by preincubating the peptide with either LPS or lipid A. These results strongly suggest that CAP37 peptide 20–44 is also a domain responsible for endotoxin binding (FIG. 8 in Pereira, et al., 1993). Further confirmation that CAP37 peptides 20–44 binds endotoxin was obtained from independent means other than inhibition of bactericidal activity. The chromogenic Limulus amebocyte lysate (LAL) assay indicated that CAP37-peptide 20–44 and 120–146 significantly neutralized LPS (See FIG. 6). A drop in absorbance indicates neutralization of LPS. Quantities of 125 µg/ml of CAP37 peptides 1–25, 20–44, and 120–146 were incubated with 0.5 ng/ml, 0.25 ng/ml and 0.1 ng/ml of LPS at 37° C. for 15 minutes and then incorporated into the LAL assay. Peptide 1–25 is ineffective. However, both peptides 20–44 and 120–146 were capable of neutralizing LPS.

Figure 7:
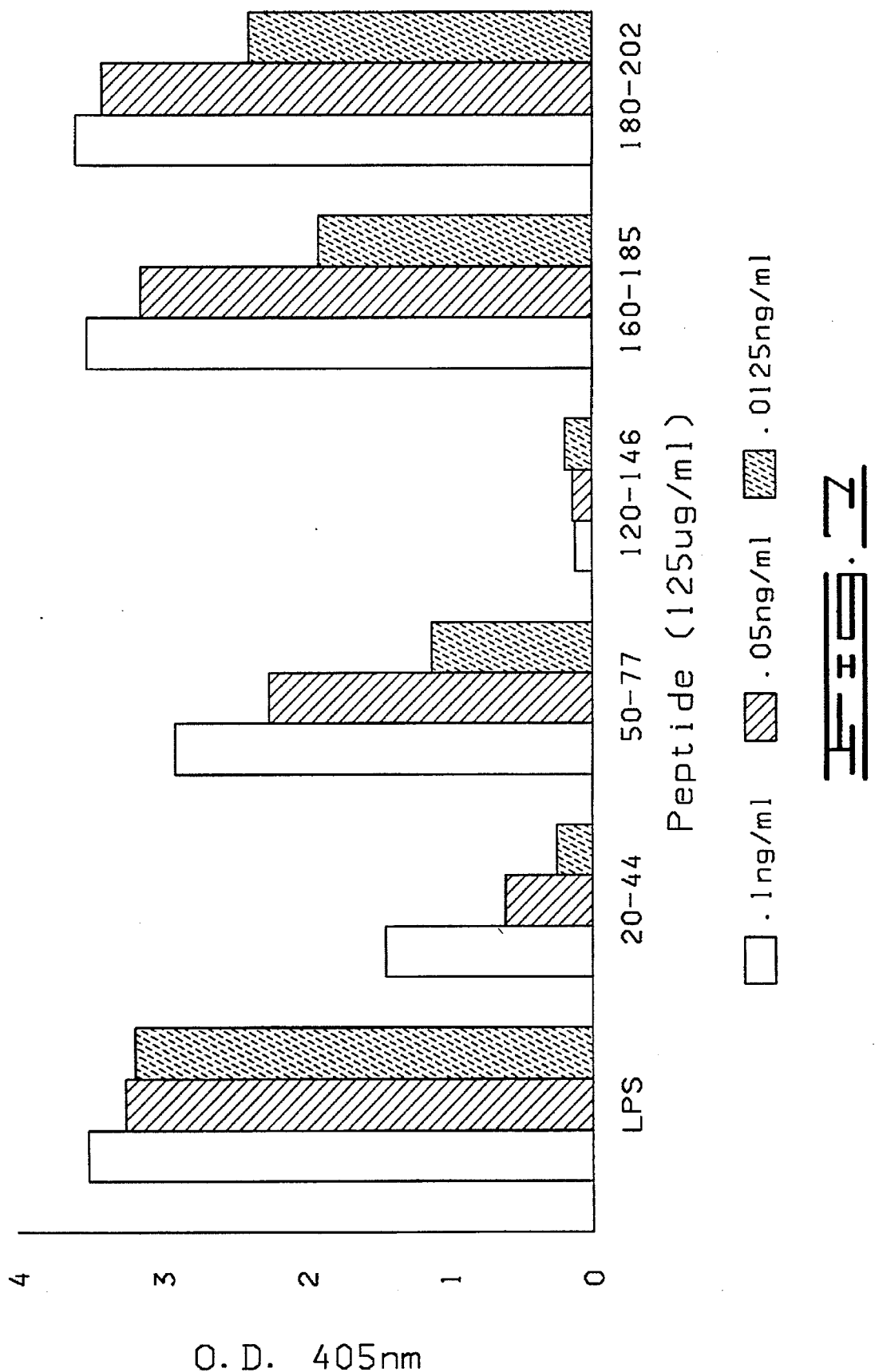
FIG. 7 is a graph showing the neutralizing effects of various CAP37 peptides against various concentrations of LPS.

FIG. 7 shows a comparison of peptide 120–146 with peptide 20–44 and other CAP37 peptides. The peptide concentration was held constant at 125 µg/ml. The LPS (wild type Salmonella minnesota was used at 0.1 ng/ml, 0.05 ng/ml and 0.0125 ng/ml. Absorbance of these concentrations of LPS alone is shown on the far left of the graph. When these concentrations of LPS were incubated with the respective peptides (20–44, 50–77, 120–146, 160–185 and 180–202) at 37° C. for 15 minutes, then incorporated into the LAL assay, a drop in the absorbance level is observed indicating neutralization, especially by CAP peptides 20–44 and 120–146.

Peptide 120–146 is especially effective in neutralizing LPS as shown in the results from an LAL assay reproduced in FIG. 8. The peptide was tested at 125 µg/ml of peptide versus LPS concentrations of 500, 125, 50, 25 and 5 ng/ml. The results indicate that peptide 120–146 is capable of binding LPS at very high LPS concentrations. Peptide 120–146 at this concentration can neutralize as much as 50 ng/ml of LPS. The series of bars on the right hand side of the graph of FIG. 8 indicate the absorbance values of LPS alone at the various concentrations.

The major benefit of using CAP37 peptides 20–44 or 120–146 over other systems that may block deleterious effects of endotoxin is that the functional binding domain of CAP37 is narrowed down to a polypeptide of about two dozen amino acids. This is a considerable reduction in size from Bactericidal Permeability-Increasing Protein (BPI) and Lipopolysaccharide Binding Protein (LBP), making the peptide more membrane permeable, and less demanding to produce synthetically. Both peptides 20–44 and 120–146 are simple to synthesize, however, peptide 120–146 is very soluble and easier to synthesize because it does not have the two cysteine residues of peptide 20–44 which also make peptide 20–44 more prone to cyclization and polymerization than peptide 120–146. Further, the antibacterial activity of BPI is directed solely against gram negative bacteria while data discussed herein indicates that CAP37 peptides 20–44 and 120–146 are active against certain gram positive bacteria as well as gram negative bacteria.

Blockage of TNFα Production

Figure 9:
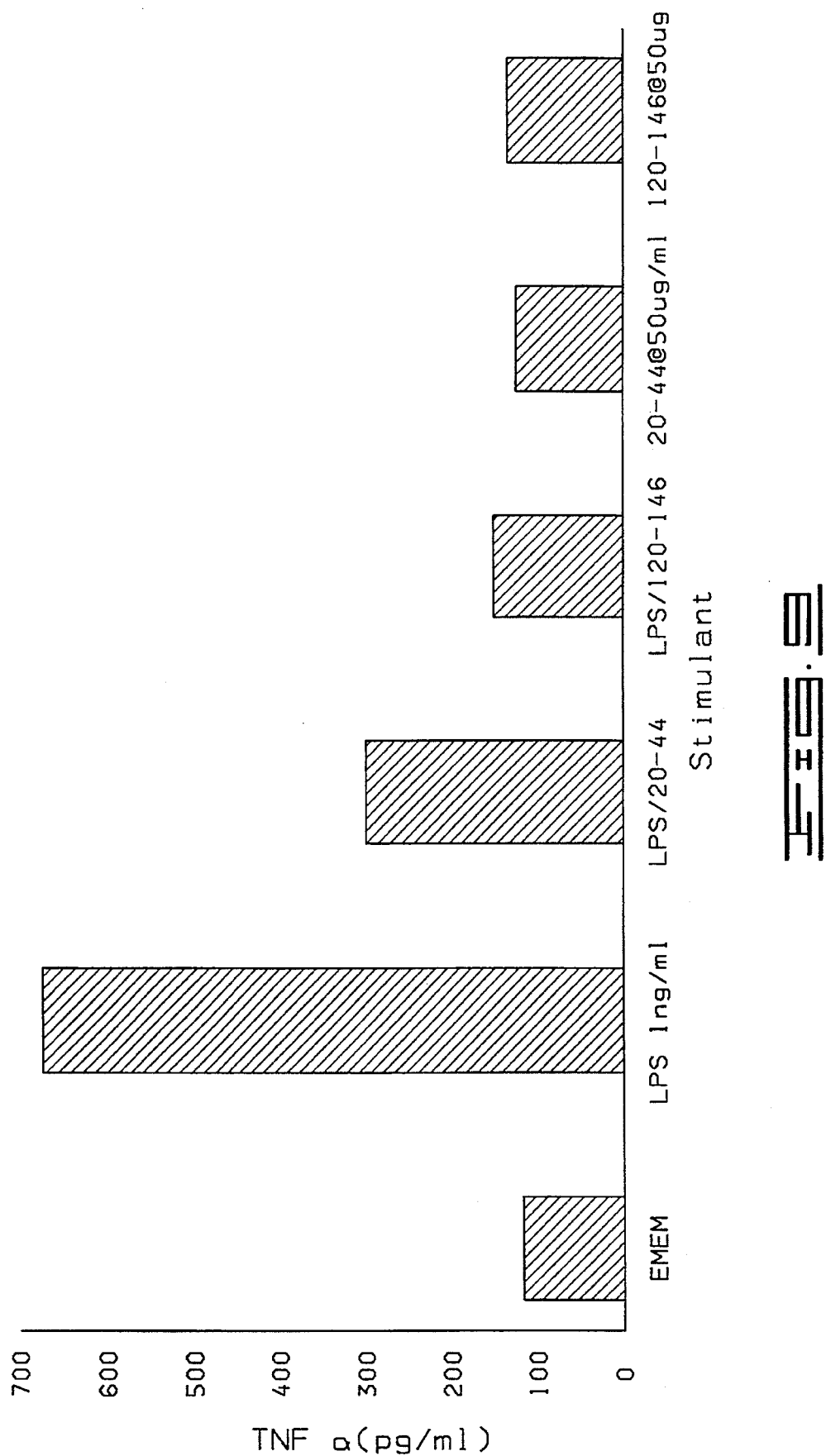
FIG. 9 is a graph showing the effect of LPS on rat macrophage TNFα production and the effects of peptides 20–44 and 20–146 on LPS-induced TNFα production in rat macrophages.

FIG. 9 shows the blocking effect of peptides 20–44 and 120–146 against the production of TNFα by rat macrophages. LPS alone, at a concentration of 1 ng/ml induces production of nearly 700 pg/ml of TNFα. When LPS is incubated for 15 minutes with peptides 20–44 or 120–146 prior to treatment of the macrophages, the production of TNFα is inhibited. TNFα is a mediator which causes many toxic effects in septic shock. The blockage of TNFα production is therefore a useful effect of these two peptides.

Attenuation of Endotoxin Effects in vivo

Hyperdynamic Model

Figure 10:
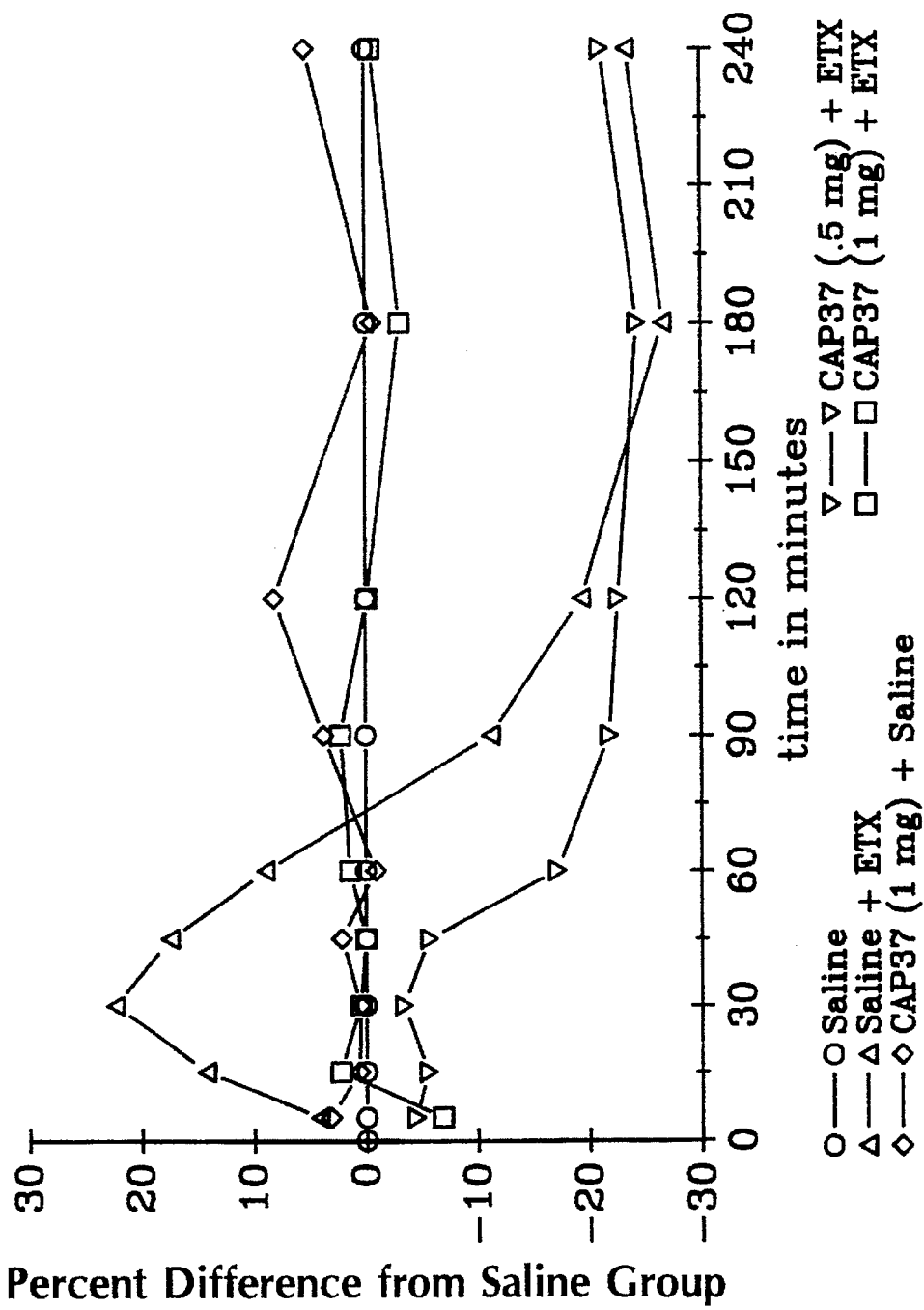
FIG. 10 is a graph comparing the effects of endotoxin and CAP37 peptide 20–44 on cardiac index in the hyperdynamic model of septic shock.
Figure 11:
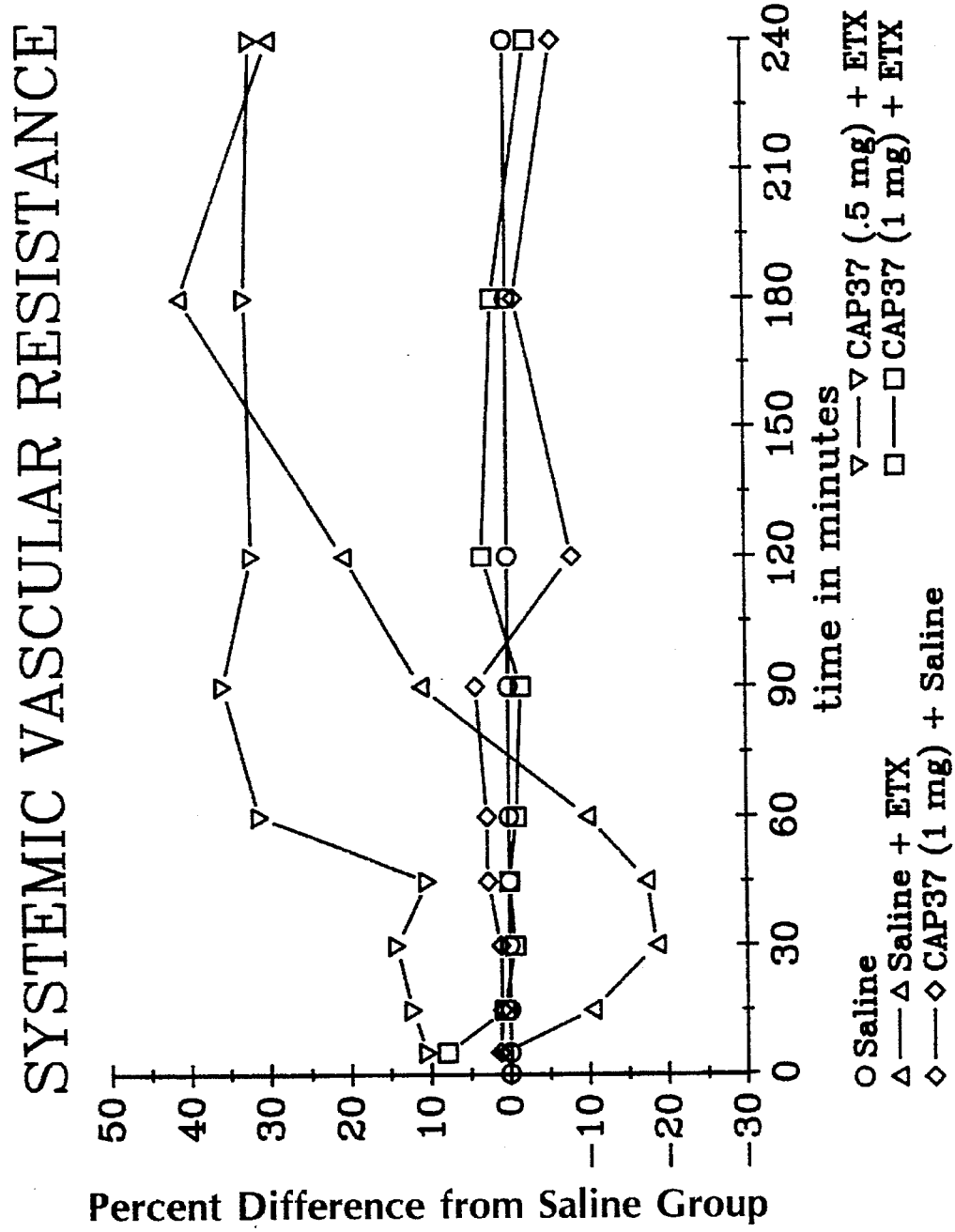
FIG. 11 is a graph comparing the effects of endotoxin and CAP37 peptide 20–44 on systemic vascular resistance in the hyperdynamic model of septic shock.
Figure 12:
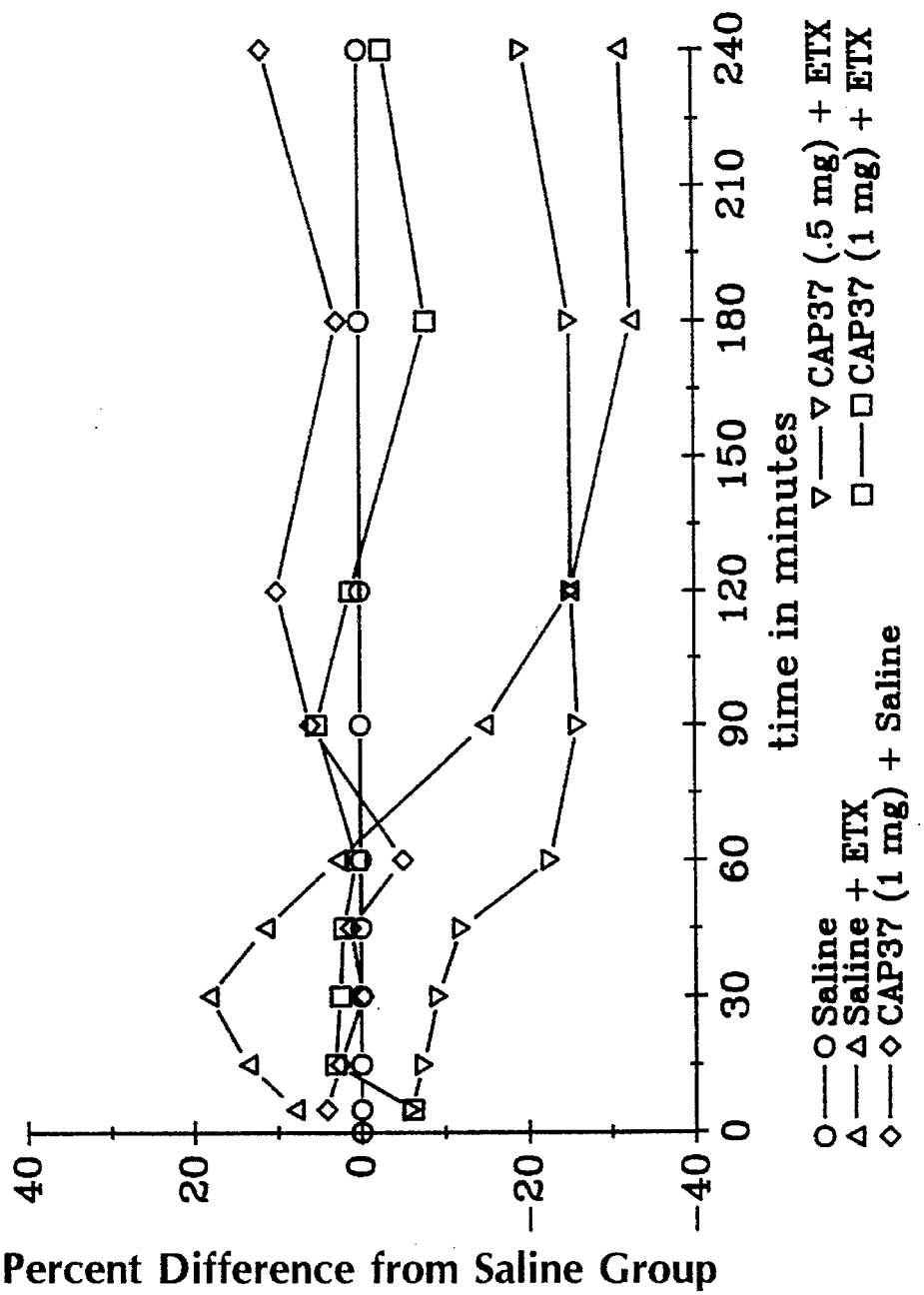
FIG. 12 is a graph comparing the effects of endotoxin and CAP37 peptide 20–44 on cardiac stroke volume in the hyperdynamic model of septic shock.
Figure 13:
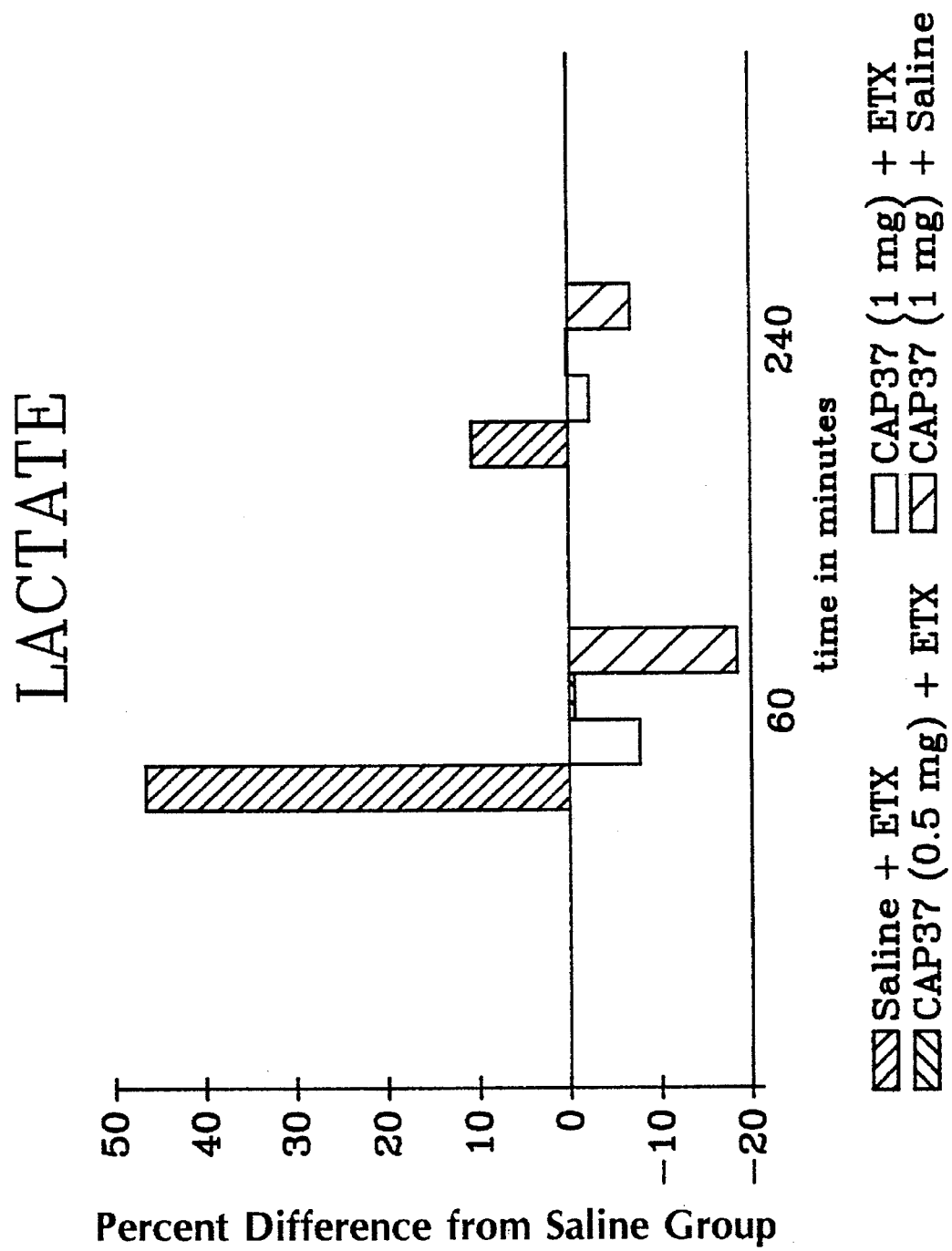
FIG. 13 is a graph comparing the effects of endotoxin and CAP37 peptide 20–44 on lactate concentration in the hyperdynamic model of septic shock.

Using a hyperdynamic model, the capacity of CAP37 peptide 20–44 to block or attenuate the in vivo effects of endotoxin (lipopolysaccharide B, E. coli 0127:B8, Sigma Chemical Co.) was evaluated by comparing the hemodynamic and metabolic responses of rats infused with 250 µg/kg of endotoxin over 30 minutes to that of rats which received the same dose of endotoxin that had been pretreated in vitro with 0.5 or 1.0 mg/kg of CAP37 peptide 20–44 prior to administration. This preliminary study contained five treatment groups: 1) saline (S)+endotoxin (ETX), 2) CAP37 peptide 20–44 (1.0 mg/kg)+ETX, 3) CAP37 peptide 20–44 (0.5 mg/kg)+ETX, 4) CAP37 peptide 20–44 (1.0 mg/kg)+ saline, and 5) saline. Each group contained 10 test animals. Control groups 4 and 5 were completely stable throughout the entire monitoring periods indicating the absence of a hemodynamic effect of CAP37 peptide 20–44 per se (see FIG. 12). In hyperdynamic shock, induced by an infusion of endotoxin (250 µg/kg) over a 30 minute time period, a 23% increase in cardiac index occurred within 30 minutes and an increase over the control was sustained for over one hour, falling to below the control value at 90 minutes, and remaining at about 20% below control for the remainder of the 4 hour monitoring period (FIG. 10). Systemic vascular resistance was essentially the mirror image of cardiac output, decreasing to about 20% of control at 30 minutes and sustaining an increase from 90 to 240 minutes reaching a peak of 40% of control at 180 minutes (FIG. 11). The response of cardiac stroke volume mimicked the cardiac output response (FIG. 12). Inadequate tissue perfusion was demonstrated by the significant increase in blood lactate concentrations indicating a shift from aerobic to anaerobic metabolism (FIG. 13). In the hyperdynamic model, injecting endotoxin into the animals has a major effect on cardiac index (FIG. 10), systemic vascular resistance (FIG. 11), and stroke volume (FIG. 12), but not on mean arterial pressure, heart rate, or respiration rate. There appears to be a slight increase in body temperature. Hematocrit and glucose concentrations were unaffected by endotoxin infusion. The circulating white blood cell count (FIG. 14) however, dropped dramatically with endotoxin infusion indicating an increase in the marginating pool and adherence to endothelial cells. The peptide 20–44 ameliorated the drop in white blood cell count. Of the parameters that changed following endotoxin infusion, (FIGS. 10–14) it is apparent that infusion of CAP37 peptide 20–44, at the higher concentration had a preventive (or blocking) effect. There was no difference between the saline controls and the group receiving the high dose of peptide. All of these endotoxin-induced responses were greatly or completely prevented by the 1.0 mg/kg dose of CAP37 peptide 20–44 and the values for this group were similar to those of the two control groups. The lower dose of peptide (0.5 mg) was not as effective. The 0.5 mg/kg dose prevented the hyperdynamic phase, but not the transition to the hypodynamic phase, which occurred about 60 minutes after infusion. This suggests a dose-effect by CAP37 peptide 20–44.

Hypodynamic Model

Figure 18:
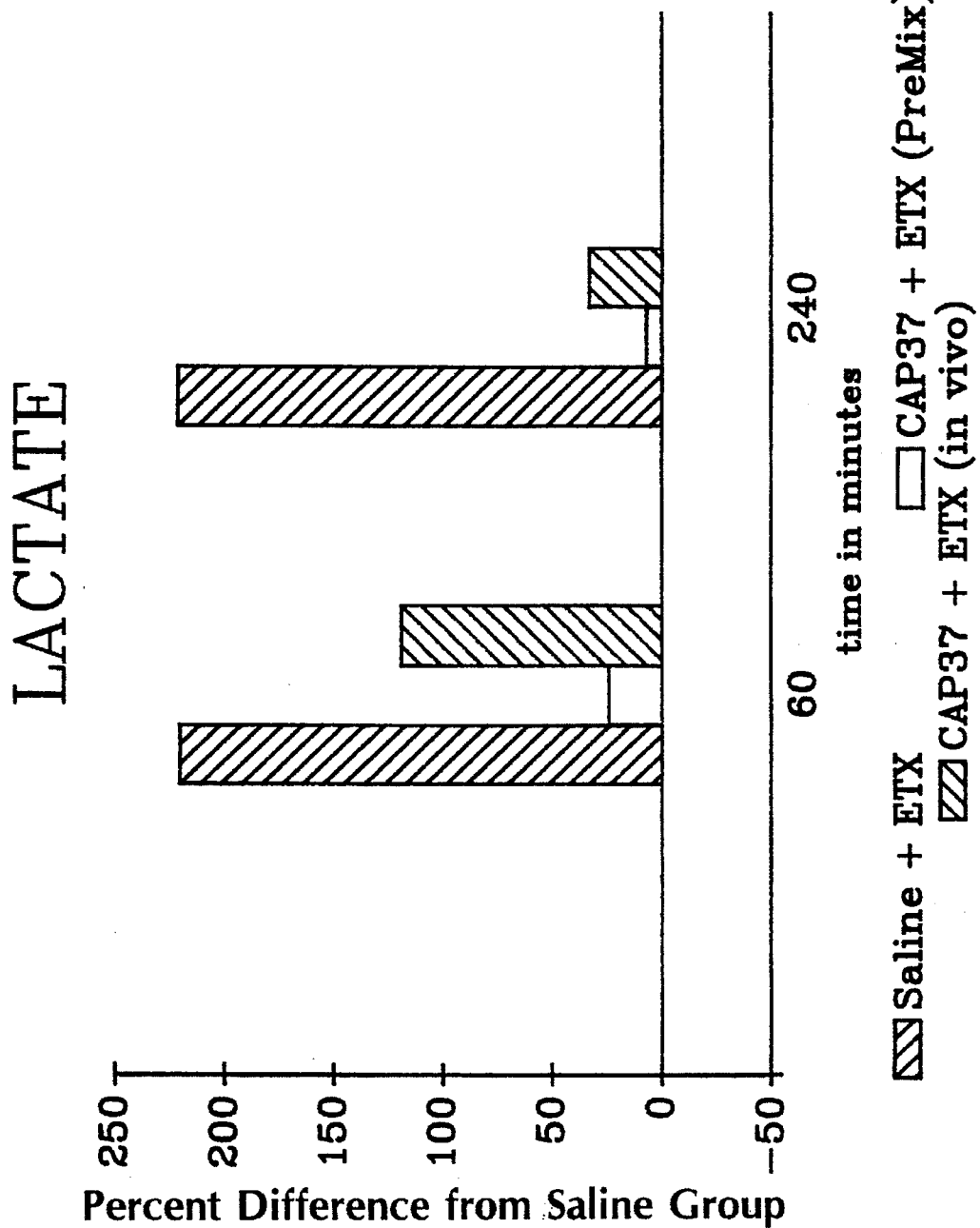
FIG. 18 is a graph comparing the effects of endotoxin and CAP37 peptide 20–44 on lactate concentration in the hypodynamic model of septic shock.
Figure 19:
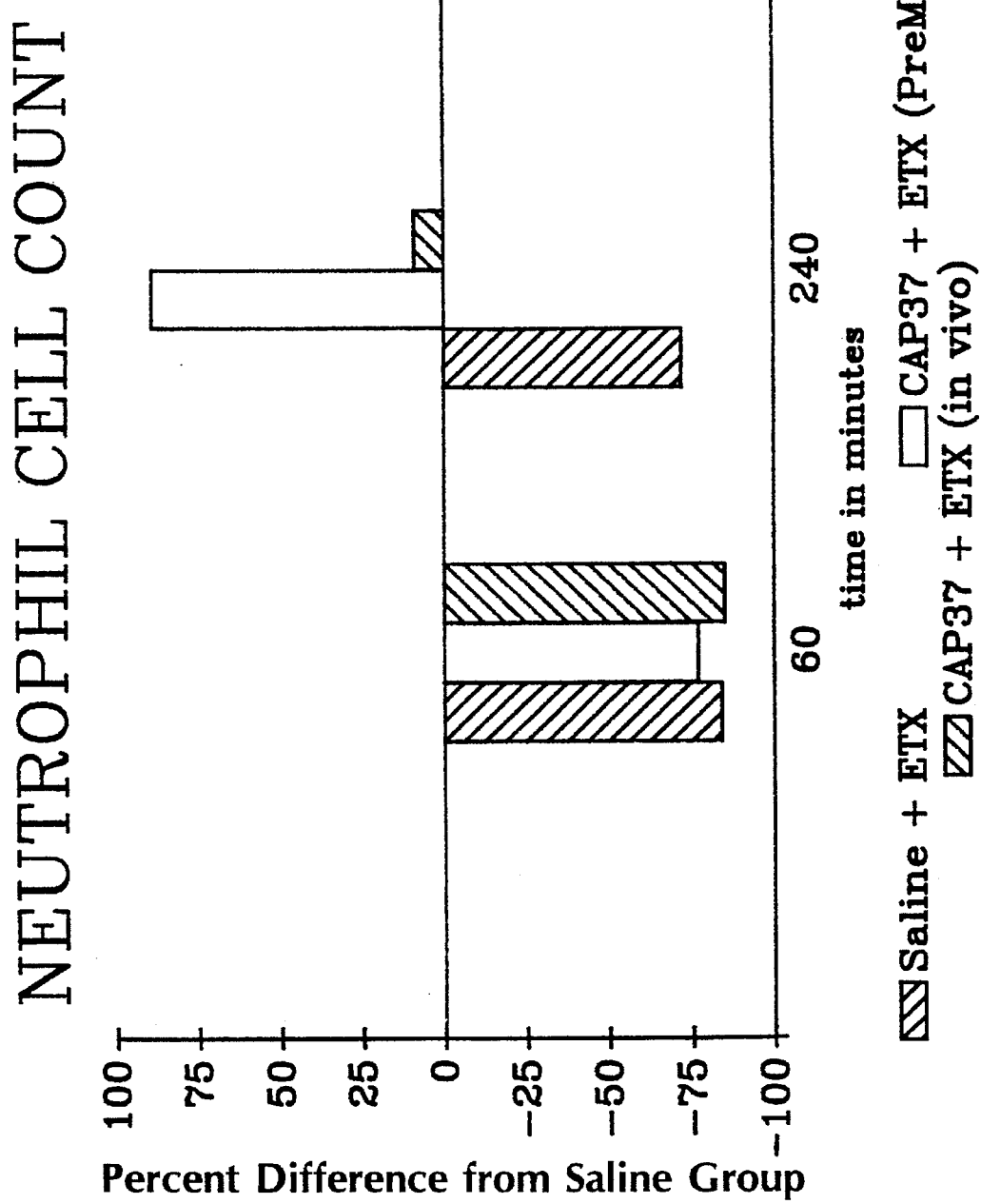
FIG. 19 is a graph comparing the effects of endotoxin and CAP37 peptide 20–44 on neutrophil cell count in the hypodynamic model of septic shock.

The ability of CAP37 peptide 20–44 to ameliorate the responses to larger doses of endotoxin (20 mg/kg) which induce hypodynamic septic shock is illustrated in FIGS. 15–19. The hypodynamic model uses an extremely high dose of endotoxin (20 mg/kg) and is given in a single bolus. This model is associated with the late stages of septic shock in the absence of fluid resuscitation. The 20 mg/kg dose is an LD90 dose, i.e. 9 of 10 animals were dead by 24 hr. Three groups were involved in this study: 1) saline 2) CAP37 peptide 20–44 (3.0 mg/kg) premixed with endotoxin before administration, 3) CAP37 peptide 20–44 infused in vivo simultaneously with endotoxin. Each group contained 5 animals. Endotoxin (20.0 mg/kg) delivered as a bolus (Group 1) elicited an intense sustained decrease in cardiac output (FIG. 15), an increase in systemic vascular resistance (FIG. 16), and a decrease in stroke volume (FIG. 17) suggesting a situation of inadequate tissue perfusion which was substantiated by significantly increased blood lactate concentrations (FIG. 18). An important characteristic of this model of endotoxic shock is a dramatic decrease in circulating neutrophils (FIG. 19) indicating margination and creating the potential for migration into the tissue. Both CAP37 peptide 20–44 treatments (Groups 2 and 3) significantly attenuated the cardiovascular disturbances and the increase in lactate concentrations which returned to or were maintained at near baseline levels. Circulating neutrophil counts had returned to normal by the end of the monitoring period in the peptide-treated groups. In this model of hypodynamic endotoxic shock a higher peptide concentration should increase the effectiveness. The results of these studies conclusively demonstrate that CAP37 peptide 20–44 has the capacity to inhibit or prevent the in vivo activity of endotoxin.

Methodology

Male Sprague-Dawley rats weighing 300±25 gms were used in this study as test animals. The rats were initially anesthetized with 5% enflurane and then intubated and connected to a rodent respirator delivering 2% enflurane. The right carotid artery was cannulated with a thermocouple-catheter combination for measurement of thermodilution cardiac output curves (Columbus Instruments, CardioMaxII-R) and aortic blood pressure and for sampling arterial blood. The thermocouple tip was placed in the aortic arch just distal to the aortic valve. The thermocouple-catheter combination was constructed by inserting a Columbus Instruments FR #1 microprobe into Tygon Micro Bore tubing (0.030 in. I.D., 0.090 in. O.D.) through a hole in the tubing wall. The microprobe was extended 1⅛ in past the end of the Micro bore tubing, and epoxy was applied to seal the hole and secure the microprobe. The microprobe was then passed through the proper length of Teflon tubing (lightweight, 24 ga) cut to allow the tip of the microprobe to extend just past the end of the Teflon tubing after the Teflon tubing had been wedged tightly into the end of the larger Tygon tubing.

The tip of one catheter (Silastic-Medical Grade tubing— 0.025 in. I.D., 0.047 in. O.D.) was placed just adjacent to the right atrium via the right jugular vein for injection of endotoxin (hypodynamic model; 20 mg/kg delivered as a bolus over 15 seconds)/treatment composition, monitoring central venous pressure, and rapid injection of room-temperature saline to produce thermodilution curves for calculation of cardiac output. Animals in the hyperdynamic model were implanted with two catheters. One catheter (Silastic-Medical Grade tubing—0.025 in. I.D., 0.047 in. O.D.) was placed just adjacent to the right atrium for monitoring central venous pressure, and to generate the thermodilution curves. An additional smaller catheter (Silastic-Medical Grade tubing—0.020 in. I.D., 0.037 in. O.D.) was also placed in the vein to deliver a continuous infusion of endotoxin (hyperdynamic model; 250 µg/kg infused over 30 minutes)/treatment composition. The proper distance for insertion of the venous and arterial catheters to achieve the optimal tip placement was determined in a series of experiments using anesthetized animals of the same sex and weight as those used in this study. At the end of each study in the conscious animals presented here, the catheters were checked visually to assure proper placement.

The catheters were guided under the skin exiting through the back of the neck just below the base of the skull. All incision areas were anesthetized (lidocaine) before surgery and again just before suturing. The animals were allowed to regain consciousness and were then placed in cages that allowed unrestrained movement about the cage at all times throughout the study with no further handling. Sixty minutes from recovery and thirty minutes before treatment, baseline control measurements were taken. Utilization of a swivel-cannulae system provided continuous measurements of central venous pressure, aortic blood pressure, and heart rate. The dose of endotoxin used for the hyperdynamic model was 250 µg/kg which was infused via a separate catheter placed in a jugular vein. The dose used for the hypodynamic model was 20 mg/kg. Cardiac outputs were measured using the thermodilution technique by rapidly injecting a volume calculated to deliver 100 µl of room temperature saline to the circulatory system. At the end of the 30 minute control period, the treatment composition was injected intravenously. Central venous and aortic blood pressures, heart rate and respiration rate were continuously monitored for the next 4 hours. Following the control readings, cardiac output measurements were made at 5, 15, 30, 60, 120, 180 and 240 minutes after treatment. Arterial blood samples were also taken for measuring TNF (Tumor necrosis factor) and IL-1 (interleukin-1), lactate, PMN counts and blood glucose. Additional details concerning the methodology of the hypodynamic model may be found in the article by D. J. Brackett, C. F. Schaefer, P. Tompkins, L. Fagraeus, L. J. Peters, and M. F. Wilson which is entitled "Evaluation of Cardiac Output, Total Peripheral Vascular Resistance, and Plasma Concentrations of Vasopressin in the Conscious, Unrestrained Rat During Endotoxemia," *Circ. Shock* 17: 273–284 (1985) which is hereby incorporated herein in its entirety by reference.

Survival of Rats Treated With Endotoxin

In order to determine in vivo efficacy of CAP37 peptides 20–44 and 120–146 in neutralizing the toxicity of endotoxin rats were injected intravenously with endotoxin 48 hours after catheterization and with varying amounts of one of peptide 20–44 or 120–146 following endotoxin injection.

Peptide 20–44

Thirteen control animals were treated with 2.5 µg of endotoxin/kg of body weight in saline plus 800 µg Actinomycin D/kg in saline. Actinomycin D is applied to increase the sensitivity of the rats to the effects of endotoxin in accordance with known methods. Lethality was recorded hourly for the first 48 hours and daily thereafter for seven days. In this study, animals alive after seven days were considered to be permanent survivors. Results are shown in Table I. Control animals (treated with saline) survived an average of 11.3 hours after injection of endotoxin. None of the control animals were alive after 24 hours. Survival times of individual rats (in hours) were: 7, 11, 9, 9, 13, 8, 11.4, 22, 13, 10, 16, 10 and 8.

Other groups were further treated with one of three levels of CAP37 peptide 20–44. Rats were injected intravenously with endotoxin and Actinomycin D (as above) followed immediately with i.v. injection of the peptide. Ten animals were injected with 0.2 mg of peptide/kg. Of these, three survived longer than 24 hours and one survived seven days. Ten animals were injected with 1.0 mg of peptide/kg. In summary, 9 of 10 animals survived longer than 24 hours and 6 of 10 survived longer than 48 hours, and 5 survived longer than 7 days.

Finally, ten animals were injected with 5.0 mg of peptide/kg of these all survived longer than 24 hours, all survived longer than 48 hours and eight survived longer than 7 days. These results clearly show a protective effect of CAP37 peptide 20–44 against the effects of endotoxin in vivo. Two control peptides were used in this study. One was a synthetic peptide based on the sequence of cathepsin G incorporating amino acid residues 20–47, which has almost 50% homology with CAP37 peptide 20–44. The other was a synthetic peptide based on the amino acid sequence of CAP37 comprising amino acid residues 180–202. Both control peptides were not effective.

TABLE 1

LETHALITY (PERCENT SURVIVAL)

| GROUP | SURVIVAL TIME | | | | |
|---|---|---|---|---|---|
| | 24 h | 48 h | 3 d | 5 d | 7 d |
| Vehicle | 0 | 0 | 0 | 0 | 0 |
| Control Peptide | 20 | 10 | 10 | 10 | 10 |
| Control Peptide CAP37P$_{20-44}$ | 20 | 10 | 10 | 10 | 10 |
| 0.2 mg/kg | 30 | 10 | 10 | 10 | 10 |
| 1.0 mg/kg | 90 | 60 | 60 | 50 | 50 |
| 5.0 mg/kg | 100 | 100 | 80 | 80 | 80 |

Peptide 120–146

In a separate experiment which followed the same protocols as above, rats were treated with CAP peptide 120–146 after injection with endotoxin. The results are shown in Table II. Animals in the control group, i.e., which received saline but no peptide, all died within 24 hours. Animals treated with 0.2 mg/kg of peptide 120–146 had 60% survival after one day and 20% survival after 5 days. Animals treated with 1.0 mg/kg of peptide 120–146 had 70% survival after one day and 40% survival after 5 days.

TABLE II

LETHALITY (PERCENT SURVIVAL)

| GROUP | SURVIVAL TIME | | | |
|---|---|---|---|---|
| | 24 h | 48 h | 3 d | 5 d |
| Vehicle CAP37P$_{120-146}$ | 0 | 0 | 0 | 0 |
| 0.2 mg/kg | 60 | 20 | 20 | 20 |
| 1.0 mg/kg | 70 | 50 | 40 | 40 |

Utility

The present invention contemplates using peptides 20–44, 120–146 and/or effective subunits thereof both to treat ongoing endotoxic (septic) shock and to prophylactically treat an individual who may have a risk of septic shock prior to a surgical procedure such as bowel or bladder surgery or surgical manipulation of other organs where gram negative bacteria normally reside and could enter the bloodstream. The peptide would be delivered, in a preferred embodiment, intravenously.

The dose would be approximately 3 mg/kg body weight. The peptide would be suspended in a suitable carrier such as normal saline at a concentration of 1 mg/ml. Thus for the average 70 kg male, this would involve a volume of 210 ml. This should be given as one infusion, intravenously over 30–60 minutes. A second infusion, may be given at 24 hours after the first infusion. Subsequent infusions over the next 72 hours could be required in the event circulating endotoxin levels are still apparent. Antibiotics, intravenous fluids, cardiovascular and respiratory support could also be provided if requested by the attending physician in a manner known to one of ordinary skill in the art.

Changes may be made in the construction and the operation of the various components, elements and assemblies described herein or in the steps or the sequence of steps of the methods described herein without departing from the spirit and scope of the invention as defined in the following claims.

What is claimed is:

1. A peptide capable of binding bacterial lipopolysaccharide, comprising the amino acid sequence as defined in the Sequence Listing of SEQ ID NO:3.

2. A DNA molecule comprising a nucleotide sequence encoding a peptide having the amino acid sequence set forth in SEQ ID NO:3, wherein said encoded peptide effectively binds to bacterial lipopolysaccharide.

3. A composition for treating septic shock in a mammal, comprising a therapeutically effective amount of a peptide having the amino acid sequence as defined in the Sequence Listing of SEQ ID NO:3.

4. A method for treating septic shock in a mammal, comprising administering to the mammal a therapeutic composition comprising a pharmacologically effective amount of a bacterial lipopolysaccharide binding peptide having the amino acid sequence as defined in the Sequence Listing by SEQ ID NO:3.

5. A method of prophylactic treatment for minimizing septic shock in a mammal, comprising administering to the mammal a therapeutic composition comprising a pharmacologically effective amount of a lipopolysaccharide binding peptide having the amino acid sequence set forth in SEQ ID NO:3.

6. A method of treating physiological effects caused by bacterial lipopolysaccharide in a mammal, comprising administering to the mammal a therapeutic composition comprising a pharmacologically effective amount of a peptide having the amino acid sequence as defined in the Sequence Listing by SEQ ID NO:3.

7. A method of treating a mammal for the effects of bacterial lipopolysaccharide on systemic vascular resistance, cardiac output, tissue perfusion and white blood cell count, comprising administering to the mammal a therapeutic composition comprising a pharmacologically effective amount of a peptide having the amino acid sequence as defined in the Sequence Listing by SEQ ID NO:3.

8. A method of mediating the effects of a bacterial lipopolysaccharide-induced endotoxic response in a test animal, comprising:

providing a test animal;

administering a predetermined amount of endotoxin to the test animal; and administering a predetermined amount of CAP37 peptide 120–146 to the test animal.

9. A method for treating infection at a particular tissue site in an animal, comprising the step of applying to the tissue site a topical medication comprising an antibiotic peptide having the amino acid sequence set forth in SEQ ID NO:3, wherein the peptide is present in the medication at a pharmacologically effective amount to treat infection.

10. The method of claim 9, wherein the form of the topical medication is selected from the group consisting of pastes, gels, creams, and ointments.

11. A method for treating infection in animals, comprising the step of administering to the animal a therapeutic composition comprising a pharmacologically effective amount of an antibiotic peptide comprising the sequence as defined in SEQ ID NO:3.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY:linear ( i i ) MOLECULE TYPE: peptide ( v ) FRAGMENT TYPE: internal ( v i ) ORIGINAL SOURCE: 20-44aa of mature CAP37 protein ( x i ) SEQUENCE DESCRIPTION: SEQ ID NO:1:

```
Asn Gln Gly Arg His Phe Cys Gly Gly Ala Leu Ile His Ala Arg Phe
1               5                   10                  15
Val Met Thr Ala Ala Ser Cys Phe Gln
            20              25
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE: 23-42aa of mature CAP37 protein ( x i ) SEQUENCE DESCRIPTION: SEQ ID NO:2:

```
Arg His Phe Cys Gly Gly Ala Leu Ile His Ala Arg Phe Val Met Thr
1               5                   10                  15
Ala Ala Ser Cys
            20
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE: 120-146aa of mature CAP37 protein ( x i ) SEQUENCE DESCRIPTION: SEQ ID NO:3:

```
Gly Thr Arg Cys Gln Val Ala Gly Trp Gly Ser Gln Arg Ser Gly Gly
1               5                   10                  15
Arg Leu Ser Arg Phe Pro Arg Phe Val Asn Val
            20                  25
```